United States Patent
Posner et al.

(10) Patent No.: US 8,884,032 B2
(45) Date of Patent: Nov. 11, 2014

(54) TRIOXANE MONOMERS AND DIMERS

(75) Inventors: Gary H. Posner, Baltimore, MD (US); Lauren E. Woodard, Baltimore, MD (US); David R. Levine, Baltimore, MD (US); Deuk Kyu Moon, Baltimore, MD (US); Bryan T. Mott, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 263 days.

(21) Appl. No.: 13/321,343

(22) PCT Filed: May 19, 2010

(86) PCT No.: PCT/US2010/035404
§ 371 (c)(1),
(2), (4) Date: Jan. 11, 2012

(87) PCT Pub. No.: WO2010/135427
PCT Pub. Date: Nov. 25, 2010

(65) Prior Publication Data
US 2012/0108545 A1    May 3, 2012

Related U.S. Application Data

(60) Provisional application No. 61/179,475, filed on May 19, 2009, provisional application No. 61/230,160, filed on Jul. 31, 2009, provisional application No. 61/262,945, filed on Nov. 20, 2009.

(51) Int. Cl.
C07D 321/00    (2006.01)
A61K 31/335    (2006.01)
C07D 493/18    (2006.01)
C07D 519/00    (2006.01)

(52) U.S. Cl.
CPC ............ *C07D 493/18* (2013.01); *C07D 519/00* (2013.01)
USPC .......................................... 549/348; 514/450

(58) Field of Classification Search
USPC .......................................... 549/348; 514/450
See application file for complete search history.

(56) References Cited

U.S. PATENT DOCUMENTS

2006/0074251 A1    4/2006    Jung
2006/0142377 A1    6/2006    Posner et al.

FOREIGN PATENT DOCUMENTS

WO    WO2007067333 A2    6/2007

OTHER PUBLICATIONS

International Artemisinin Study Group, "Artesunate combinations for treatment of malaria: meta-analysis", The Lancet • vol. 363 • Jan. 3, 2004, 9-17.
Elizabeth A. Ashley, et al., "Artemisinin-based combinations", Current Opinion in Infectious Diseases 2005, 18:531-536.
Yearick, Kimberly et.al., "Overcoming Drug Resistance to Heme-Targeted Antimalarials by Systematic Side Chain Variation of 7-Chloro-4-aminoquinolines", J. Med. Chem. 1008, 51, 1995-1998.
Jefford, Charles W., "Synthetic Peroxides as antimalarials", Current Opinion in Investigational Drugs 2004 5(8):866-872.

(Continued)

*Primary Examiner* — Andrew D Kosar
*Assistant Examiner* — Raymond Covington
(74) *Attorney, Agent, or Firm* — Ward and Smith, P.A.

(57) ABSTRACT

Monomeric and dimeric trioxane fluoroaryl amides, 5-carbon-linked, C-10 non-acetal trioxane dimer esters; trioxane silylamides; and trioxane dimer orthoesters and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

16 Claims, 2 Drawing Sheets

(56) References Cited

OTHER PUBLICATIONS

Woodard, Lauren E., et al., "Malaria-infected Mice Live until at least day 30 after a New Monomeric Trioxane Combined with Mefloquine Are Administered Together in a single Low Oral Dose", J. Med. Chem. 2009, 52, 7458-7462.

Olliaro, Piero L. et al., "Clinical public health implications of antimalarial drug resistance, Antimalarial Chemotherapy: Mechanisms of Action, Resistance, and New Directions in Drug Discovery", Humana Press Inc. 2001, Totowa NJ.

"Guidelines for the treatment of malaria", Guidelines for guidelines, Geneva, World Health Organization, 2003 (document EIP/GPE/EQC/2003.1.

Tang, Yuanqing, et al., "Synthetic Peroxides as Antimalarials", College of Pharmacy, University of Nebraska Medical Center, Omaha, Nebraska, Medicinal Research Reviews, vol. 24, No. 4, 425-448, 2004.

Tenter, Astrid M., et al., "*Toxoplasma gondii*: from animals to humans", International Journal for Parasitology 30 (2000) 1217-1258.

Jonathan L. Vennerstrom, et al., "Identification of an antimalarial synthetic trioxolane drug development candidate", Nature, vol. 430, Aug. 19, 2004.

E. Fully Torrey, et al., "Antibodies to *Toxoplasma gondii* in Patients With Schizophrenia: A Meta-Analysis", Schizophrenia Bulletin, vol. 33, No. 3 pp. 729-736-, 2007.

Issaka Sagara, et al., "A Randomized Trial of Artesunate-Mefloquine versus Artemether-Lumefantrine for Treatment of Uncomplicated *Plasmodium falciparum* Malaria in Mali" Am. J. Trop. Med. Hyg., 79(5), 2008, pp. 655-661.

Aurelia Souarea, et al., "Factors related to compliance to anti-malarial drug combination: example of amodiaquine/sulphadoxine-pyrimethamine among children in rural Senegal", Malaria Journal 2009, 8:118.

Sodiomon B. Sirima, et al., "The efficacy and safety of a new fixed-dose combination of amodiaquine and artesunate in young African children with acute uncomplicated *Plasmodium falciparum*", Malaria Journal 2009, 8:48.

Issaka Sagara, et al., "Efficacy and safety of a fixed dose artesunate-sulphamethoxypyrazine-pyrimethamine compared to artemether-lumefantrine for the treatment of uncomplicated *falciparum* malaria across Africa: a randomized multi-centre trial", Malaria Journal 2009, 8:63.

Andrew S. Rosenthal, et al., "Malaria-Infected Mice Are Cured by a Single Oral Dose of New Dimeric Trioxane Sulfones Which Are Also Selectively and Powerfully Cytotoxic to Cancer Cells", J. Med. Chem. 2009, 42 (4), 1198-1203.

Gary H. Posner, et al., "Malaria-Infected Mice Are Cured by a Single Dose of Novel Artemisinin Derivatives", J. Med. Chem 2007, 50, 2516-2519.

Sandhya Ramanathan-Girish, et al., "Pharmacokinetics of the Antimalarial Drug, AQ-13, in Rats and *Cynomolgus macaques*", International Journal of Toxicology, 23:179-189, 2004.

Robert G. Ridley, "Medical need, scientific opportunity and the drive for antimalarial drugs", Nature, vol. 415, Feb. 2002.

Gary H. Posner, et al., "Malaria-Infected Mice Are Cured by Oral Administration of New Artemisinin Derivatives", J. Med. Chem. 2008, 51, 1035-1042.

Paul M. O'Neill, et al., "A Medicinal Chemistry Perspective on Artemisinin and Related Endoperoxides", J. Med. Chem. 2004, vol. 47, No. 12.

O Y Ke, et al., "Inihibition of growth of *Toxoplasma gondii* by qinghaosu and derivates", Antimicrobial Agents and Chemotherapy, vol. 34, No. 10, Oct. 1990, p. 1961-1965.

Ik-Hyeon Paik, et al., "Second Generation, Orally Active, Antimalarial, Artemisinin-Derived Trioxane Dimers with High Stability, Efficacy, and Anticancer Activity", J. Med. Chem, 2006, 27431-2734.

Gary H. Posner, et al., "Orally Active, Antimalarial, Anticancer, Artemisinin-Derived Trioxane Dimers with High Stability and Efficacy", J. Med. Chem 2003, 46, 1060-1065.

Kailash C. Pandy, et al., "Independent Intramolecular Mediators of Folding, Activity, and Inhibition for the *Plasmodium falciparum* Cysteine Protease Falcipain-2", The Journal of Biological Chemistry, vol. 279, Vo. 5, Issue of Jan. 30, pp. 3484-2491, 2004.

Ralph LeBlanc, et al., "Markedly enhanced immunogenicity of a Pfs25 DNA-based malaria transmission-blocking vaccine by in vivo electroporation", Vaccine (2008) 26, 185-192.

Ai Jeng Lin, et al., "Antimalarial Activity of New Water-Soluble Dihydroartemisinin Derivatives", J. Med. Chem. 1987, 30, 2147-2150.

H.Y. Myint, et al., "Efficacy and safety of dihydroartemisinin-piperaquine", Transactions of the Royal Society of Tropical Medicine and Hygiene (2007) 101, 858-866.

Deuk Kyu Moon, et al., "Antimalarial Preclinical Drug Development: A Single Oral Dose of a 5-Carbon-linked Trioxane Dimer Plus Mefloquine Cures Malaria-Infected Mice", Drug Dev Res. Jan. 1, 2009; 71(1): 76-81.

Daniel L. Klayman, "An Antimalarial Drug from China", Science, New Series, vol. 228, No. 4703 (May 31, 1985), pp. 1049-1055.

Jane X. Kelly, et al., "Discovery of dual function acridones as a new antimalarial chemotype", Nature, vol. 459| May 14, 2009.

Mankil Jung, et al., "Antitumor Activity of Novel Deoxoartemisinin Monomers, Dimers, and Trimer", J. Med. Chem. 2003, 46, 987-994.

Lorraine Jones-Brando, et al., "Drugs used in the treatment of schizophrenia and bipolar disorder inhibit the replication of *Toxoplasma gondii*", Science Direct, Schizophrenia Research 62, (2003) 237-244.

E. Holfels, et al., "In vitro effects of artemisinin ether, cycloguanil hydrochloride (alone and in combination with sulfadizine), quinine sulfate, mefloquine, primaquine phosphate, trifluoperazine hydrochloride, and verapamil on *Toxoplasma gondii*", Antimicrob. Agents Chemother. 1994, 38(6):1392.

Richard K. Haynes, "From Artemisinin to New Artemisinin Antimalarials: Biosynthesis, Extraction, Old and New Derivatives, Stereochemistry and Medicinal Chemistry Requirements", Current Topics in Medicinal Chemistry, 2006, vol. 6, 509-537.

Fraser Hof, et al., "Starving the Malaria Parasite: Inhibitors Active against the Aspartic Proteases Plasmepsins I, II, and IV", Angew. Chem. Int. Ed. 2006, 45, 2138-2141.

Jean-Paul Guthmann, et al., "Short Report: High Efficacy of two artemisinin-based combinations (Artesunate + Amodiaquine and Artemether + Lumefantrine) in Caala, Central Angola", Am. J. Trop. Med. Hyg., 75(1), 2006, pp. 143-145.

Michael H. Gelb, "Drug discovery for malaria: a very challenging and timely endeavor", Current Opinion in Chemical Biology 2007, 11:440-445.

Stephen Gately, et al., "Novel Therapeutics With Enhanced Biological Activity Generated by the Strategic Introduction of Silicon Isosteres into Known Drug Scaffolds", Drug Development Research 68:156-163 (2007).

C.I. Fanello, et al., "A randomised trial to assess the safety and efficacy of artemether—lumefantrine (Coartem®) for the treatment of uncomplicated *Plasmodium falciparum* malaria in Rwanda", Transactions of the Royal Society of Tropical Medicine and Hygiene (2007) 101, 344-350.

Anirudh Gautam, et al., "Pharmacokinetics and Pharmacodynamics of Endoperoxide Antimalarials", Current Drug Metabolism, 2009, 10, 289-306.

Richard T. Eastman, et al., "Artemisinin-based combination therapies: a vital tool in efforts to eliminate malaria", Nature, Dec. 2009, vol. 7, pp. 864-874.

Fernando de Pilla Varotti, et al., "Synthesis, Antimalarial Activity, and Intracellular Targets of MEFAS, a New Hybrid Compound Derived from Mefloquine and Artesunate", Antimicrobial Agents and Chemotherapy, Nov. 2008, p. 3868-3874.

Randolph L. Berens, et al., "Selection and Characterization of *Toxoplasma gondii* Mutants Resistant to Artemisinin", Concise Communications JID 1998: 177 (Apr.), pp. 1129-1131.

(56) References Cited

OTHER PUBLICATIONS

H.R. Chang, et al., "In vitro effects of three new 1,2,4-trioxanes (pentatroxane, thiahexatroxane, and hexatroxanone) on *Toxoplasma gondii*", Antimicrobial Agents and Chemotherapy, 1989, 33(10):1748.

Xiaochun Chen, et al., "Inhibitors of *Plasmodium falciparum* methionine aminopeptidase 1b possess antimalarial activity", PNAS, Sep. 26, 2006, vol. 103. No. 39, 14548-14553.

James Chadwick, et al., "Synthesis and biological evaluation of extraordinarily potent C-10 carba artemisinin dimers against *P. falciparum* malaria parasites and HL-60 cancer cells", Bioorganic & Medicinal Chemistry 17 (2009 1325-1338.

Emmanual Arinaitwe, et al., "Artemether-Lumefantrine versus Dihydroartemisinin-Piperaquine for *falciparus* Malaria: A Longitudinal, Randomized Trial in Young Ugandan Children", Drug Therapy for Malaria in Ugandan Children, CID 2009:49 (Dec. 1), 1629-1637.

Aurelien Bigot, et al., "A Convenient Allylic Functionalization of Bis(prop-2-enyl)methanol by Direct Trimetalation", Synthesis 2008, No. 22, pp. 3692-3696.

Jean-Pierre Begue, et al., "Fluoroartemisinins: Metabolically More Stable Antimalarial Artemisinin Derivatives", ChemMedChem 2007, 2, 608-624.

S. Bachmann, et al., "Psychopathology in First-Episode Schizophrenia and Antibodies to *Toxoplasma gondii*", Psychopathology 2005: 38-87-90.

TRIOXANE MONOMERS AND DIMERS

CROSS-REFERENCE TO RELATED APPLICATIONS

This application is a 35 U.S.C. §371 U.S. national entry of International Application PCT/US2010/035404 having an international filing date of May 19, 2010, which claims the benefit of U.S. Provisional Application Nos. 61/179,475, filed May 19, 2009; 61/230,160, filed Jul. 31, 2009; and 61/262,945, filed Nov. 20, 2009, the contents of each of the aforementioned applications is herein incorporated by reference in its entirety.

FEDERALLY SPONSORED RESEARCH OR DEVELOPMENT

This invention was made in part with United States Government support under AI 34885 awarded by the National Institutes of Health (NIH). The U.S. Government has certain rights in the invention.

BACKGROUND

Malaria is one of the world's most widespread infectious diseases. Ridley et al., 2002. Much effort is currently being devoted to develop effective vaccines to prevent humans from becoming infected with malaria parasites. LeBlanc et al., 2008; Troye-Blomberg et al., 2007. Treatment of humans afflicted with malaria with antimalarial amines, such as chloroquine, has been effective for over 50 years. Ridley et al., 2002. Malaria parasites, however, have developed widespread resistance to popular quinoline-based antimalarial drugs, including chloroquine. Olliaro et al., 2001. Such resistance seriously compromises the efficacy of chloroquine for treating people infected with malaria and has stimulated a search for new natural and synthetic antimalarial agents.

Progress in chemotherapeutic methods of treating humans afflicted with malaria has been made using protease inhibitors to starve the parasites, Hof et al., 2006; Pandey et al., 2004; using antimalarial acridones, Kelly et al., 2009, and new 4-aminoquinolines, Yearick et al., 2008, to counteract resistance; and using some modified chloroquine analogs. Ramanathan-Girish et al., 2004. A new non-quinoline family of rapidly acting antimalarial peroxides was discovered in China during the early 1970s and has since become popular in treating malaria in humans. Bégué and Bonnet-Delepon, 2007; Gelb, 2007; Haynes, 2006; Jefford, 2004; Klayman, 1985; O'Neill and Posner, 2004; Shizhen, 2003; Tang et al., 2004. The natural trioxane artemisinin and its semi-synthetic derivative trioxanes artemether and water-soluble sodium artesunate are now recommended by the World Health Organization (WHO) for use in combination with a classical antimalarial amine drug for reliable chemotherapy of humans infected with malaria. WHO, 2006. This artemisinin combination therapy (ACT) is now widely used in areas of the world where malaria is endemic. Ashley and White, 2005; de Pilla Varotti et al., 2008; Adjuik et al., 2004; Guthmann et al., 2006; Myint et al., 2007; Sirima et al., 2009.

Typically, current ACT requires a repeated dose regimen, which usually involves a total of three to six doses of a trioxane plus an amino antimalarial administered to a malaria-infected patient over several days. Sagara et al., 2008; Fanello et al., 2007. Patient compliance with adhering to such a repeated-dose regimen, however, is often a serious challenge. Souares et al., 2009. Patient compliance would be improved and cost lowered by a single dose oral cure. Therefore, a single-dose oral cure for malaria is highly desirable.

SUMMARY

The presently disclosed subject matter provides monomeric and dimeric trioxane fluoroaryl amides; 5-carbon-linked, C-10 non-acetal trioxane dimer esters; trioxane sylylamides, and trioxane dimer orthoesters and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

In some aspects, a compound of formula (I) is provided:

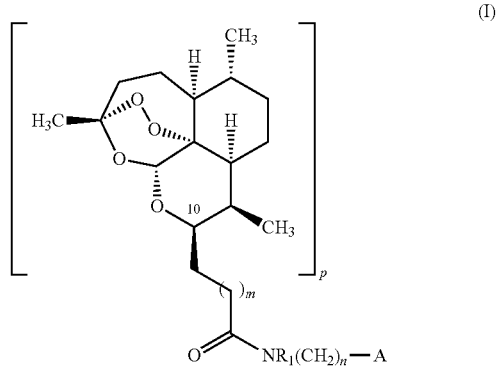

(I)

wherein:
  m is an integer from 0 to 3;
  n is an integer from 0 to 4;
  p is an integer from 1 to 2;
  $R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
  A is selected from the group consisting of a halogen-substituted phenyl; substituted or unsubstituted heteroaryl; and —Si($R_2$)$_3$, wherein each $R_2$ is independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
  or an enantiomer, diastereomer, racemate or pharmaceutically acceptable salt, prodrug, or solvate thereof.

In other aspects, a compound of formula (II) is provided:

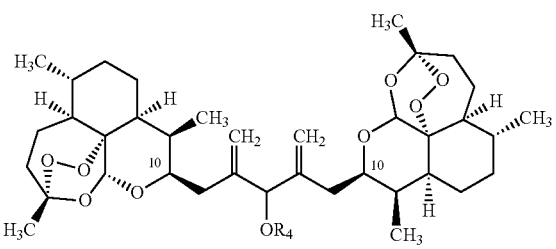

(II)

wherein:
  $R_4$ is hydrogen or —C(=O)—Ar; wherein Ar is substituted or unsubstituted aryl or substituted or unsubstituted heteroaryl;

or an enantiomer, diastereomer, racemate or pharmaceutically acceptable salt, prodrug, or solvate thereof.

In certain aspects, the presently disclosed compounds of formula (I), formula (II), or formula (III) can be used for preventing, controlling or treating an infectious disease in a subject in need of treatment thereof. In particular aspects, the infectious disease includes a parasitic disease selected from the group consisting of a plasmodia parasite infection, a *T. gondii* infection, a trypanosome parasite infection, and a cryptosporidium parasite infection. In other aspects, the method of treatment further comprises administering to the subject a quinoline anti-malarial drug including, but not limited to, chloroquine, quinine, mefloquine, and primaquine, concurrently or sequentially with a compound of formula (I), formula (II), or formula (III).

In other aspects, the presently disclosed subject matter provides a method of treating a psychiatric disorder associated with *toxoplasma* infection, such as schizophrenia, in a subject in need of treatment thereof, the method comprising administering to the subject a therapeutically-effective amount of a compound of formula (I), formula (II), or formula (III). In yet other aspects, the method further comprises administering to the subject one or more antipsychotic drugs selected from the group consisting of chlorpromazine (THORAZINE®), haloperidol (HALDOL®), fluphenazine (PROLIXIN®), thiothixene (NAVANE®), trifluoperazine (STELAZINE®), perphenazine (TRILAFON®), and thioridazine (MELLARIL®), clozapine (CLOZARIL®), risperidone (RISPERDAL®), olanzapine (ZYPREXA®), quetiapine (SEROQUEL®), ziprasidone (GEODON®), and aripiprazole (ABILIFY®) concurrently or sequentially with the compound of formula (I), formula (II), or formula (III).

In further aspects, the presently disclosed subject matter provides a method for treating cancer, including, but not limited to, leukemia, non-small cell lung cancer, colon cancer, central nervous system cancer, melanoma cancer, ovarian cancer, renal cancer, prostate cancer, and breast cancer, in a subject in need of treatment thereof, the method comprising administering to the subject a therapeutically-effective amount of a compound of formula (I), formula (II), or formula (III).

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
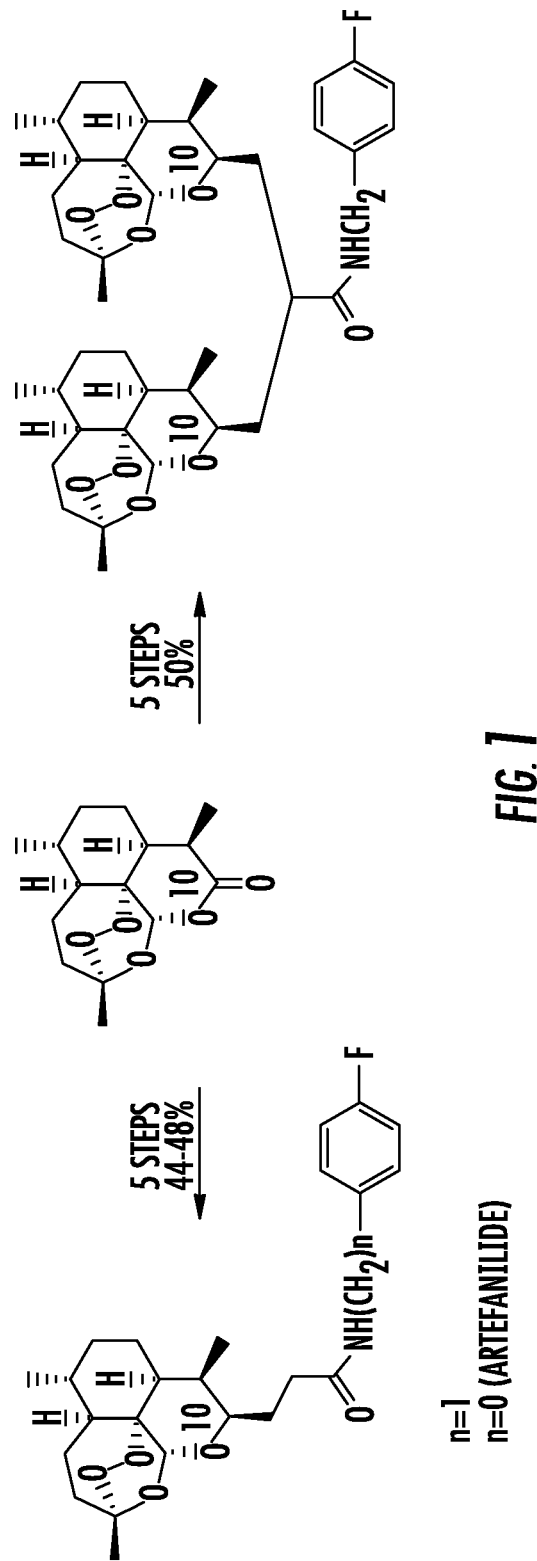
Figure 2:
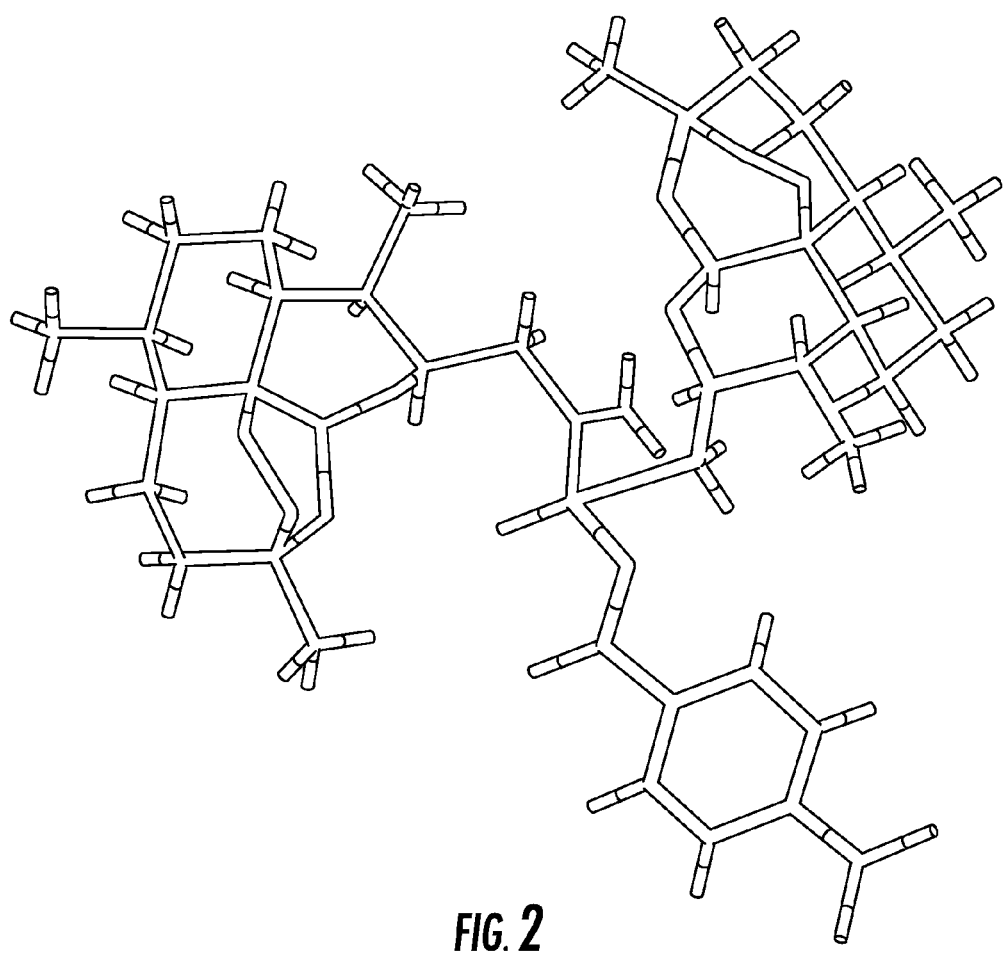

Having thus described the presently disclosed subject matter in general terms, reference will now be made to the accompanying Drawings, which are not necessarily drawn to scale, and wherein:

FIG. 1 is a general scheme for synthesizing representative presently disclosed monomeric and dimeric trioxane fluoroaryl amides; and FIG. 2 is an X-ray structure of a representative 5-carbon-linked, C-10 non-acetal trioxane dimer ester, e.g., nitrobenzoate 12a.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

As provided in more detail immediately herein below, the presently disclosed subject matter provides monomeric and dimeric trioxane fluoroaryl amides; 5-carbon-linked, C-10 non-acetal trioxane dimer esters; trioxane silylamides; and trioxane dimer orthoesters and methods of their use for treating subjects infected with malaria or other parasitic infectious diseases including, but not limited to, toxoplasmic infection; subjects afflicted with psychiatric conditions associated with toxoplasmic infection; and subjects afflicted with cancer.

I. Monomeric and Dimeric Trioxane Fluoroaryl Amides

As shown in FIG. 1, in some embodiments, the presently disclosed subject matter provides monomeric and dimeric trioxane fluoroaryl amides, which can be prepared in five steps with a relatively high yield.

A. Representative Embodiments

Referring now to Scheme 1, natural trioxane 1 derivatives, such as artemether (2b) or sodium artesunate (2c), typically are used in current regimens for treating subjects infected with malaria. One leading ACT drug for chemotherapy of humans infected with malaria is a fixed 1:6 combination of trioxane 2b (artemether) with the amino-alcohol lumefantrine (shown in Scheme 1). See Sagara et al., 2008. Typically, a six-dose adult regimen requires a total of approximately 320 mg of trioxane 2b and 1,920 mg of lumefantrine. A second ACT drug requires a three-dose adult regimen totaling 600 mg of trioxane 2c (sodium artesunate) and 750 mg of the quinoline antimalarial agent mefloquine (also shown in Scheme 1). Patient compliance with adhering to a repeated dose regimen, however, is often a serious problem. Therefore, a single dose oral cure is highly desirable. Toward this goal, a "proof of principle" advance in malaria chemotherapy using a single 144 mg/kg oral dose cure of malaria-infected mice by a new trioxane dimer sulfone carbamate has been reported. Rosenthal et al., 2009.

Scheme 1. Synthesis of monomeric and dimeric trioxane fluoroaryl amides.

2a, R = H
2b, R = CH$_3$ (β)
2c, R = C(O)CH$_2$CH$_2$COONa (α)
2d, R = C(O)CH$_3$ 4a, n = 1
4b, n = 0 (artefanilide)

Mefloquine

Lumefantrine

More particularly, referring again to Scheme 1, the presently disclosed subject matter describes the preparation and testing of the in vivo antimalarial efficacies of the fluoroaryl amide trioxane dimer 3, of the corresponding trioxane monomer fluoroaryl amide 4a, and of the trioxane monomer fluoroanilide 4b (artefanilide).

Monomeric trioxane fluoroanilide 4b is the most efficacious of the trioxane monomer fluoroaryl amides disclosed herein. For example, using only one single-digit oral dose of this new trioxane monomer combined with a three-fold higher amount of mefloquine hydrochloride prolonged survival of malaria-infected mice until at least day 30. The total amount of fluoroanilide 4b and mefloquine hydrochloride needed to achieve this single oral dose high efficacy compares favorably with the amounts of the antimalarial trioxane drugs 2b and 2c plus amine currently used clinically in repeated oral dose human ACT chemotherapy (see Scheme 1). Sagara et al., 2008.

Further, the thermally and hydrolytically stable trioxane fluoroanilide 4b can be prepared in only five simple steps and 48% overall yield from the natural trioxane artemisinin. As provided in more detail herein below, all of the malaria-infected mice lived until at least day 30 post-infection upon receiving one oral dose of only 6.8 mg/kg of monomeric trioxane 4b combined with 20 mg/kg of mefloquine hydrochloride. Of the five mice in this surviving group, four (80%)

were completely cured (no parasites in their blood) and one mouse had 4% blood parasitemia. Importantly, the efficacy of this ACT chemotherapy using monomeric trioxane 4b plus mefloquine hydrochloride is considerably better than the efficacy under the same conditions using the popular trioxane drug artemether plus mefloquine hydrochloride.

Thus, in some embodiments, the presently disclosed subject matter provides a compound of formula (I):

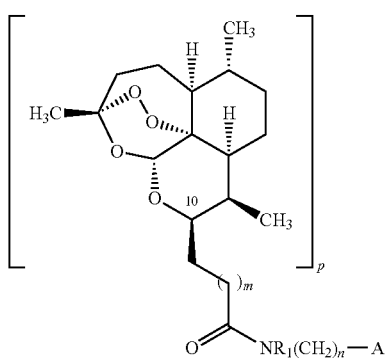

wherein:
m is an integer from 0 to 3;
n is an integer from 0 to 4;
p is an integer from 1 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
A is selected from the group consisting of a halogen-substituted phenyl and substituted or unsubstituted heteroaryl; or an enantiomer, diastereomer, racemate or pharmaceutically acceptable salt, prodrug, or solvate thereof.

In some embodiments, A is a halogen-substituted phenyl and the compound of formula (I) has the following formula:

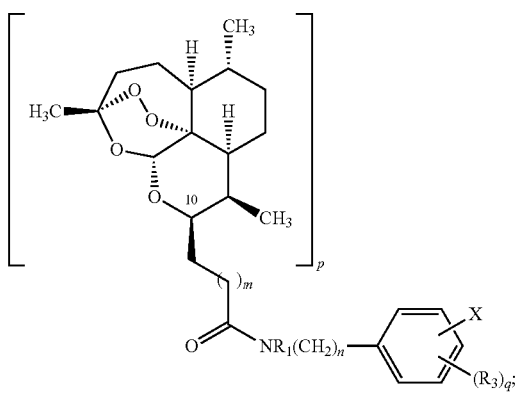

wherein:
q is an integer from 0 to 4;
X is halogen; and each occurrence of $R_3$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl.

In particular embodiments, the compound of formula (I) is selected from the group consisting of:

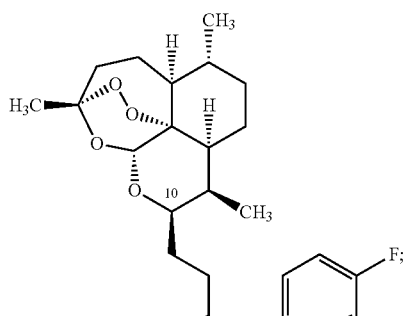

In yet other embodiments of compounds of formula (I), A is selected from the group consisting of 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

In such embodiments, the compound of formula (I) includes compounds having the following structures:
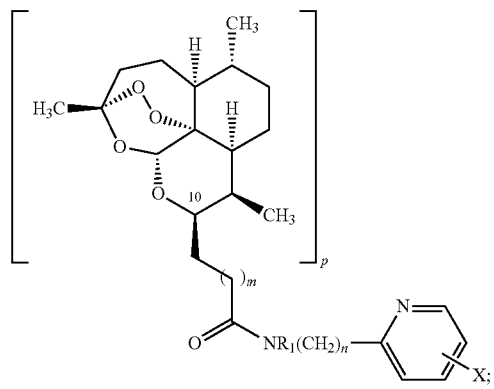
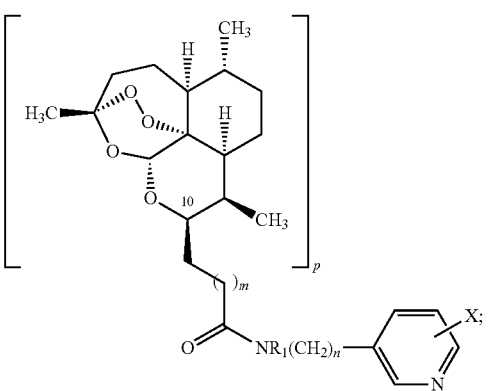
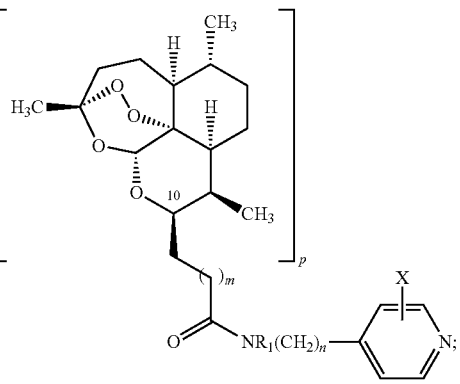
wherein X is halogen. In preferred embodiments, the halogen is fluorine.
In particular embodiments, the compound of formula (I) is selected from the group consisting of:
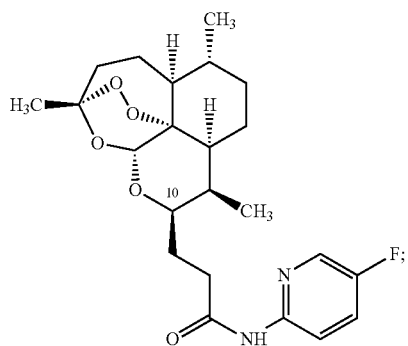
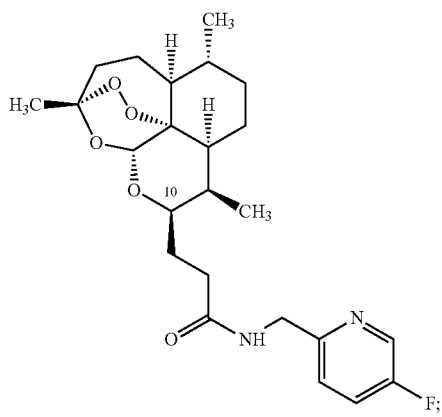
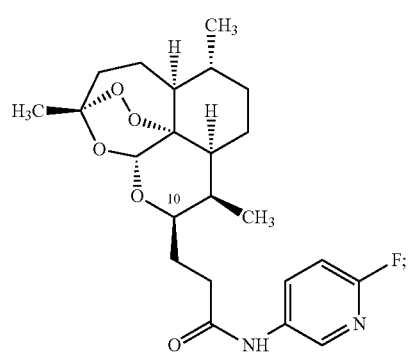
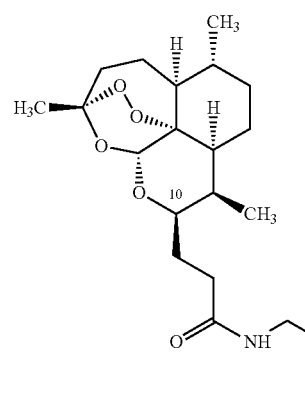
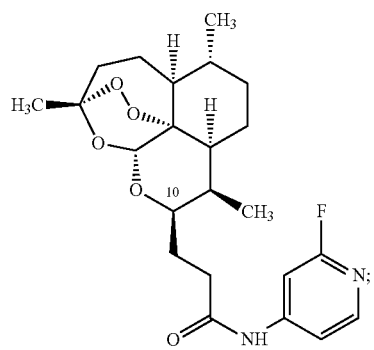

11
-continued
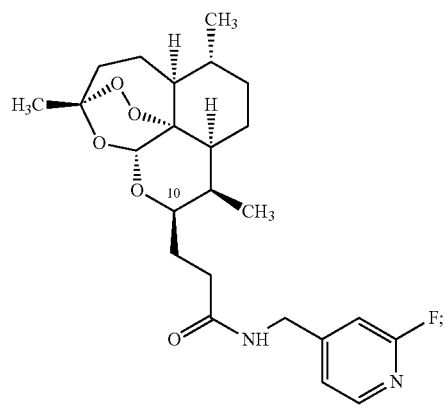
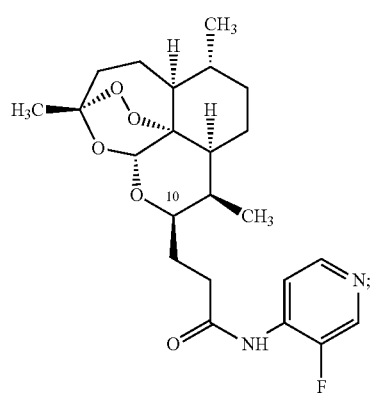
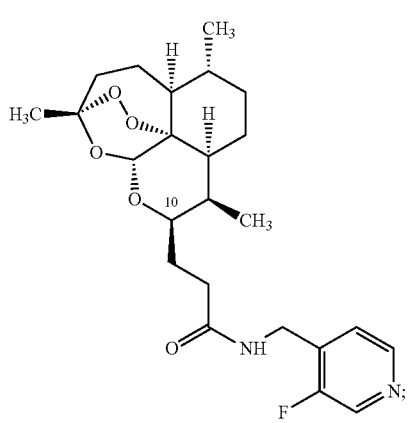
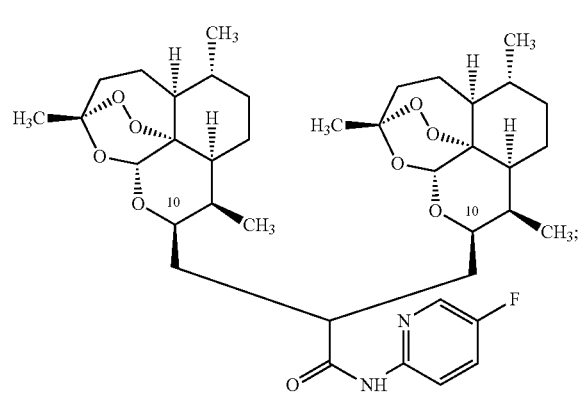
12
-continued
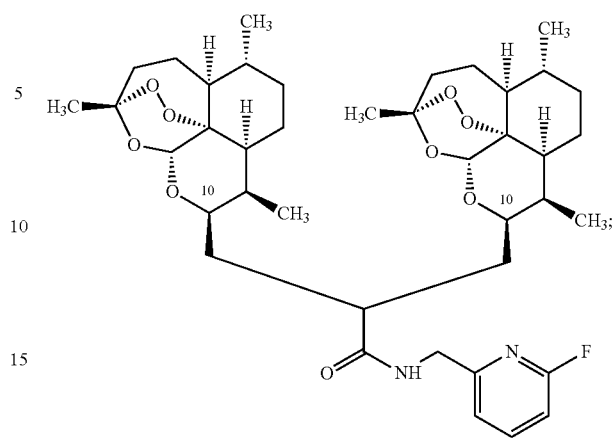
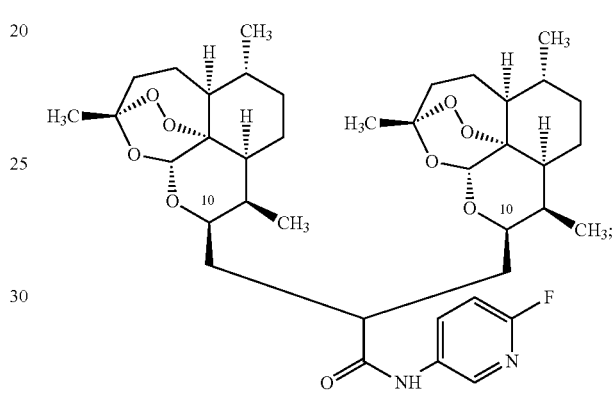
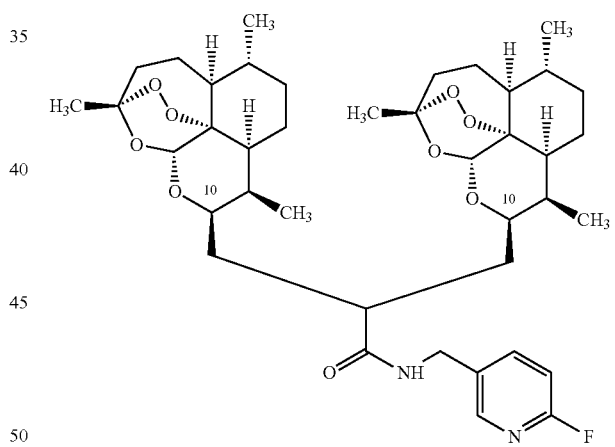
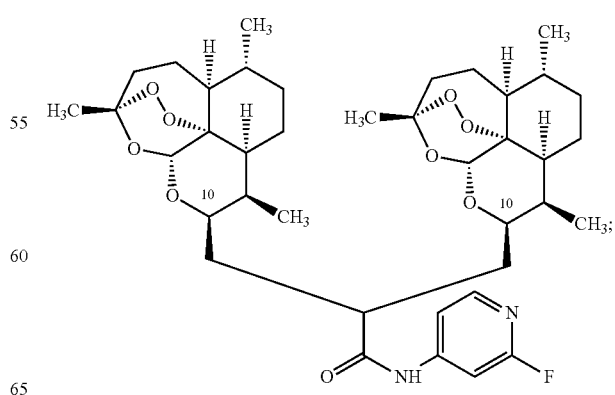

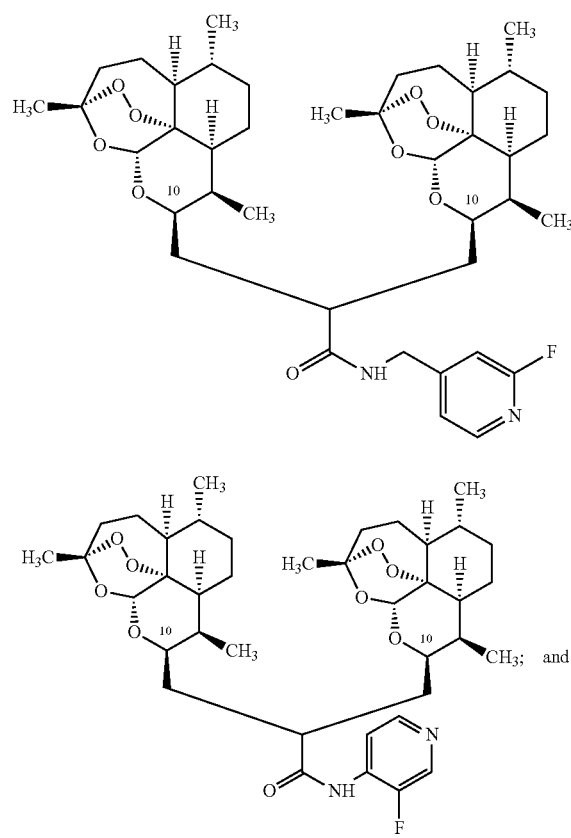
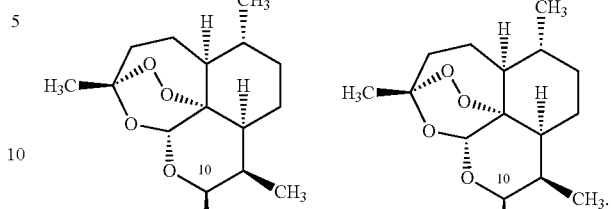
B. Chemistry
Referring now to Scheme 2, monomeric trioxane dihydroartemisin C-10 acetate (2d) was converted into dimeric trioxane 5 and then into dimer carboxylic acid 6. Posner et al., 2003. Facile amidation produced trioxane dimer fluoroaryl amide 3.
Scheme 2. Synthesis of a representative trioxane dimer fluoroaryl amide.
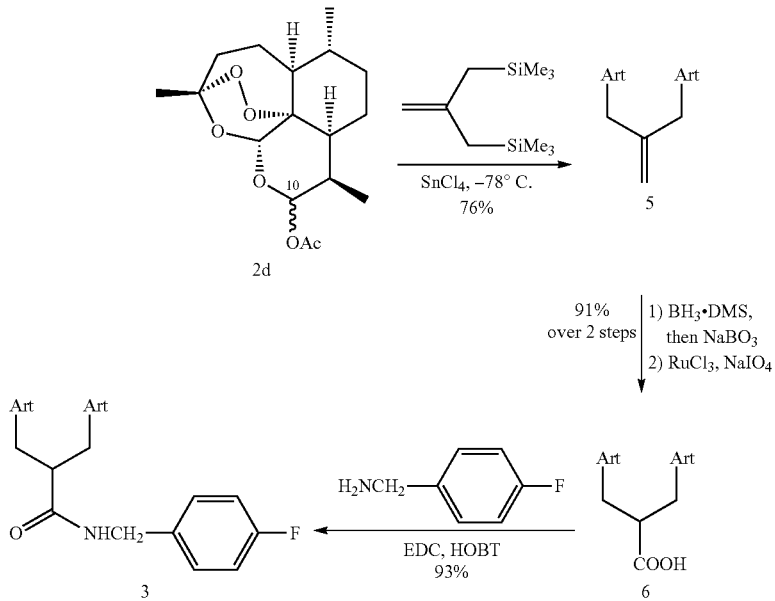

Referring now to Scheme 3, C-10 acetate 2d was converted into C-10-allyl derivative 7 and then, via hydroboration followed by oxidation, into monomeric trioxane carboxylic acid 8. Jung et al, 2003. Monomeric trioxane carboxylic acid 8 can be transformed in one step directly into a diverse library of monomeric trioxane amides. Jung et al, 2003. For example, one-step amidation of carboxylic acid 8 produced trioxane fluoroaryl amide 4a, a monomeric version of dimer fluoroaryl amide 3 (Scheme 3). In the same way, monomer trioxane fluoroanilide 4b was prepared directly and in good yield from carboxylic acid 8 (Scheme 3). The overall yield of 4b is approximately 48% from natural trioxane 1, and scale up to multigram or even kilogram amounts is expected to be straightforward. Fluoroanilide 4b is stable as a solid in the absence of solvent for at least 7 days at 60° C. and for at least 1 day at 70° C. Because amides 3, 4a, and 4b also are C-10 non-acetal trioxanes, they are all more hydrolytically stable than the C-10 acetal trioxane drugs 2b and 2c.

both widely accepted as measures of a drug's efficacy in antimalarial drug development. Three days after infection, an average of 16% blood parasitemia was observed in the control (no drug) group. Animals receiving no drug died on days 6-7 post-infection. A widely accepted yardstick of cure (i.e., 100% efficacy) is survival of animals to day 30 post-infection, with no detectable malaria parasites in the animal's blood at that time.

Average survival results are summarized in Table 1, including single oral doses of 13 mg/kg of trioxane combined with 13 mg/kg of mefloquine hydrochloride. The clinically used monomeric water-soluble trioxane drug 2c and the synthetic trioxolane peroxide drug development candidate OZ277 (9) maleate are included as monotherapy reference compounds.

As demonstrated from the data in Table 1, all three of the presently disclosed trioxane fluorinated amides 3, 4a, and 4b plus mefloquine hydrochloride prolonged average survival Scheme 3. Synthesis of a representative monomer trioxane fluoroaryl amide 4a and monomer trioxane fluoroanilide 4b.

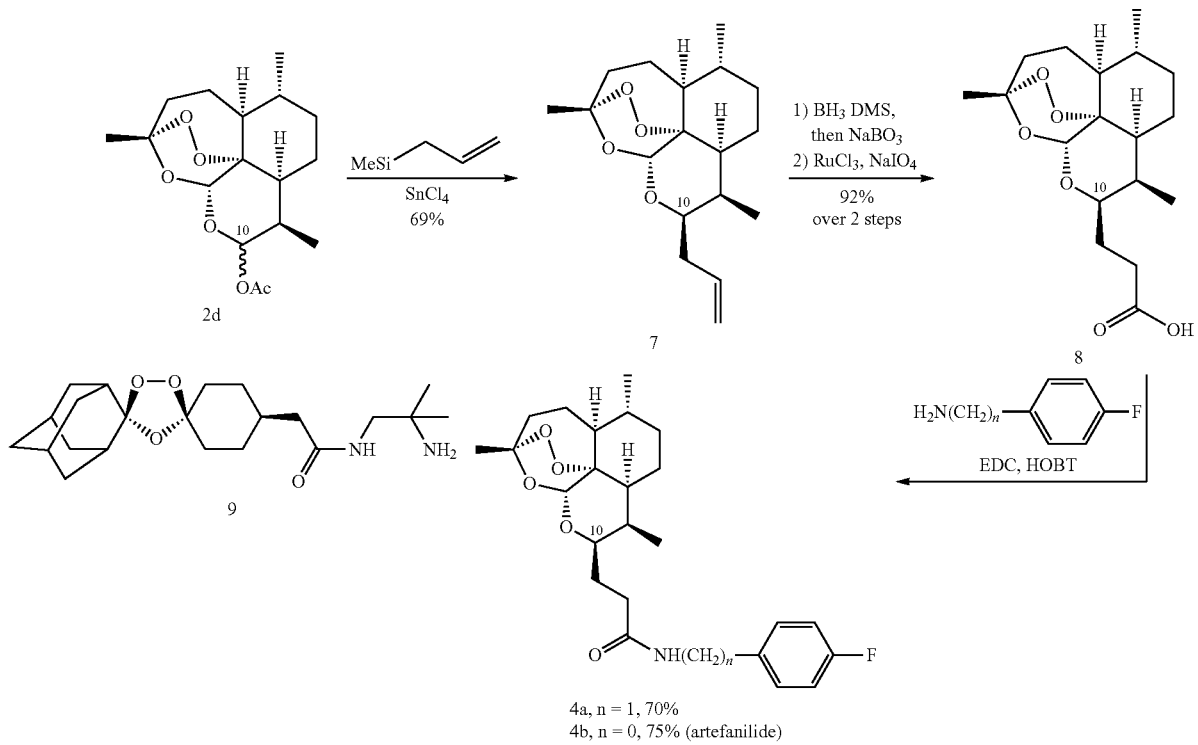

4a, n = 1, 70%
4b, n = 0, 75% (artefanilide)

C. Biology

Each trioxane 2b, 3, 4a, and 4b (0.90 mg) was dissolved in 0.11 mL of 7:3 Tween 80:ethanol and then diluted with 1.10 mL of water for oral administration to 5-week old C57BL/6J male mice (from the Jackson Laboratory) weighing about 22 g that were infected intraperitoneally on day 0 with the *Plasmodium berghei*, ANKA strain ($2 \times 10^7$ parasitized erythrocytes). Chen et al., 2006.

Each of five mice in a group was treated orally 24 h post-infection with a single dose of 0.20 mL (0.20 mL/1.21 mL×0.9 mg=0.15 mg) of diluted compound solution, corresponding to a dose of 6.8 mg/kg, combined with 20 mg/kg of mefloquine hydrochloride. Determining blood parasitemia levels, as well as monitoring the duration of animal survival compared to survival time of animals receiving no drug, are time much more effectively than monotherapy using trioxolane 9, which is in phase II clinical trials. Vennerstrom et al., 2004.

A nonfluorinated version of dimeric trioxane fluoroaryl amide 3 was much less antimalarially efficacious than fluoroaryl amide 3 (data not shown). It also is apparent from the data in Table 1 that the monomeric trioxane fluoroanilide 4b, at a single oral dose of only 6.8 mg/kg plus 20 mg/kg of mefloquine hydrochloride, was the most efficacious at prolonging survival. Of the five mice in this 30-day surviving group, four (80%) were completely cured (no parasites in their blood) on day 30 post-infection and one mouse had 4% blood parasitemia. This trioxane fluoroanilide 4b caused a 99.0% suppression of parasitemia on day 3 post-infection. A single oral dose of 13 mg/kg of trioxane fluoroanilide 4b combined with 13 mg/kg of mefloquine hydrochloride also prolonged survival of all of the mice until day 30, with four mice cured and one mouse having 2% blood parasitemia. Reinfection of the four cured mice on day 32 after the original infection caused an extended survival time, approximately four days longer than the average survival time of a newly infected control group; the mechanism(s) for this protective effect of trioxane fluoroanilide 4b against malaria reinfection is not clear at this time.

TABLE 1

Antimalarial Efficacy Using a Single Oral Dose of Trioxane Combined with Mefloquine Hydrochloride in *Plasmodium berghei*-Infected Mice

| Trioxane | Oral Dose | | Average Survival (days) After Infection | % Suppression of Parasitemia (on day 3 post-infection) |
|---|---|---|---|---|
| | Trioxane (mg/kg) | Mefloquine Hydrochloride (mg/kg) | | |
| 2b | 6.8 | 20 | 19.8 (16, 17, 21, 22, 23)[a] | 99.8 |
| 2b | 13 | 13 | 19.6 (16, 17, 21, 22, 22)[a] | 99.7 |
| 3 | 6.8 | 20 | 27.4 (22, 25, 30, 30, 30)[a] | 99.5 |
| 3 | 13 | 13 | 24.6 (17, 21, 25, 30, 30)[a] | 99.9 |
| 4a | 6.8 | 20 | 27.8 (22, 27, 30, 30, 30)[a] | 99.9 |
| 4a | 13 | 13 | 26.4 (21, 23, 26, 30, 30)[a] | 99.6 |
| 4b | 6.8 | 20 | 30 | 99.0 |
| 4b | 13 | 13 | 30 | 99.6 |
| 4b | 72 | 0 | 24.4 (21, 23, 24, 27, 27)[a] | 99.0 |
| Controls | | | | |
| Vehicle (no drug) | 0 | 0 | 6.4 (6, 6, 6, 7, 7)[a] | 0 |
| 2c | 30 | 0 | 7.6[b] | —[c] |
| 9 | 30 | 0 | 10.7[b] | 99.95[b] |
| Mefloquine | 0 | 20 | 17.6 | 99.6 |

[a]Actual mouse survival until day;
[b]Data fom Supporting Information in Vennerstrom et al. using a single oral dose of 30 mg/kg;
[c]Dash indicates "not measured."

In monotherapy control experiments, a single high oral dose (72 mg/kg) of the trioxane fluoroanilide 4b prolonged average survival until day 24.4, and a single oral dose (20 mg/kg) of mefloquine hydrochloride alone prolonged average survival to day 17.6. In an ACT control experiment, 6.8 mg/kg of the popular trioxane drug 2b combined with 20 mg/kg of mefloquine hydrochloride prolonged average survival to only day 19.8 (Table 1). Neither overt toxicity nor behavioral change attributable to trioxane drug administration was observed in any of the malaria-infected animals cured by trioxane fluoroanilide 4b plus mefloquine hydrochloride combination. The water-soluble monomeric trioxane antimalarial drug 2c and the trioxolane antimalarial drug candidate 9, although able to lower parasitemia levels considerably by day 3 post-infection, were not efficacious in prolonging the mouse average survival time beyond day 11 when used as monotherapy at a dose of 30 mg/kg.

D. Summary

In summary, a single-digit oral dose of any one of the three presently disclosed trioxane fluorinated amides 3, 4a, and 4b combined with mefloquine hydrochloride is considerably more antimalarially efficacious than the popular ACT trioxane drug 2b combined with mefloquine hydrochloride. Sagara et al., 2009; Gautam et al., 2009. Monomer trioxane fluoroanilide 4b stands out as being the most powerful antimalarial in the presently disclosed series of representative semisynthetic trioxane fluoroaryl amides.

II. 5-Carbon-Linked Trioxane Dimer Esters

In an effort toward addressing the challenging and medically urgent goal of developing a single-dose cure for malaria, a series of trioxane dimers has been reported previously, Chadwick et al., 2009; Jung et al., 2003, including some that are able to cure malaria-infected mice after only a single subcutaneous dose, Posner et al., 2007; a related series of trioxane dimers curative after three oral doses, Posner et al., 2007, 2008; and more recently a trioxane dimer sulfone curative after only a single oral dose. Rosenthal et al., 2009. A new monomeric trioxane fluoroanilide curative after only one single-digit oral dose combined with mefloquine hydrochloride also has been described. Woodard et al., 2009.

A. Representative Embodiments

In some embodiments, three new 5-carbon-linked trioxane dimer carboxylate esters have been prepared from the natural trioxane, artemisinin, in only three steps and 40-50% overall yields. Each one of these new chemical entities is at least as efficacious as the clinically used trioxane antimalarial drug artemether when combined with mefloquine hydrochloride in a low single oral dose cure.

Referring now to Scheme 4, the presently disclosed subject matter provides a family of 5-carbon-linked, C-10 non-acetal trioxane dimer esters 12 able to cure malaria-infected mice after only a single 7.1 mg/kg oral dose combined with mefloquine hydrochloride. These 5-carbon-linked trioxane dimer esters 12, produced in only three steps and 40-50% overall yields from the natural compound 1, complement previous studies on 3-carbon-linked, Posner et al., 2003, and 4-carbon-linked, Paik et al., 2006, trioxane dimers.

Scheme 4. Synthesis of representative 5-carbon-linked, C-10 non-acetal trioxane dimer esters.

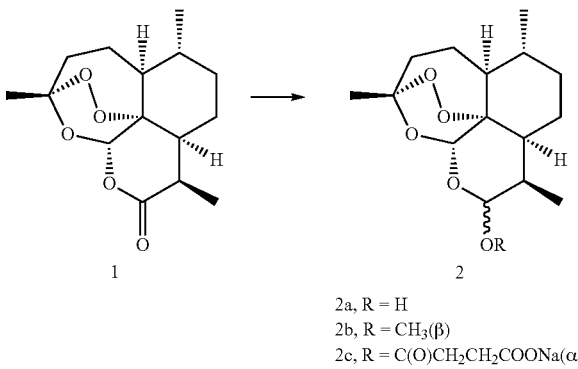

2a, R = H
2b, R = CH$_3$(β)
2c, R = C(O)CH$_2$CH$_2$COONa(α)

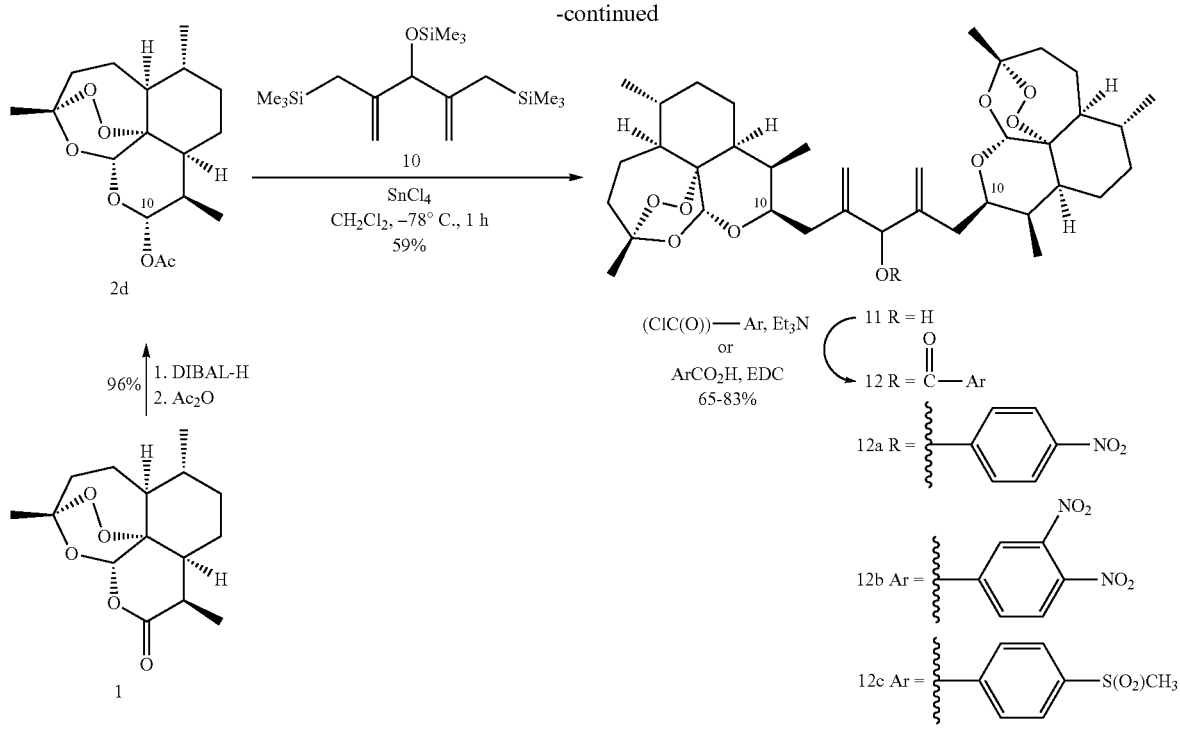

Thus, in some embodiments, the presently disclosed subject matter provides a compound of formula (II):

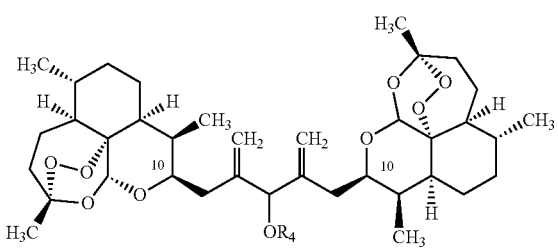

(II)

wherein:

R$_4$ is hydrogen or —C(=O)—Ar; wherein Ar is substituted or unsubstituted aryl or substituted or unsubstituted heteroaryl;

or an enantiomer, diastereomer, racemate or pharmaceutically acceptable salt, prodrug, or solvate thereof.

In certain embodiments, Ar is selected from the group consisting of:

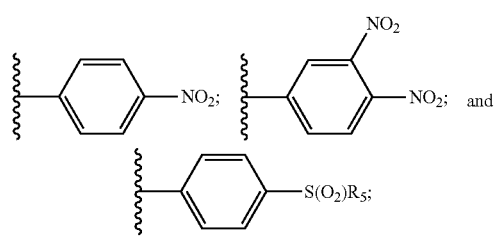

wherein R$_5$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl.

In particular embodiments, the compound of formula (II) is selected from the group consisting of:

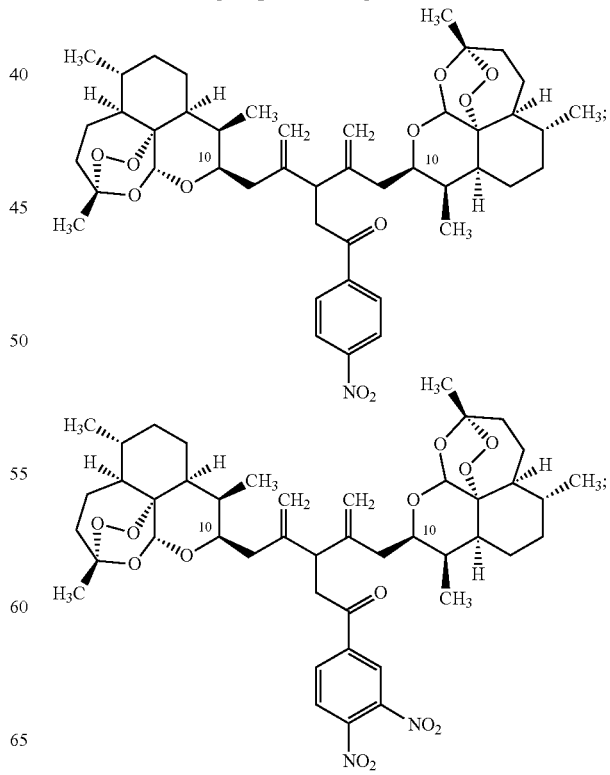

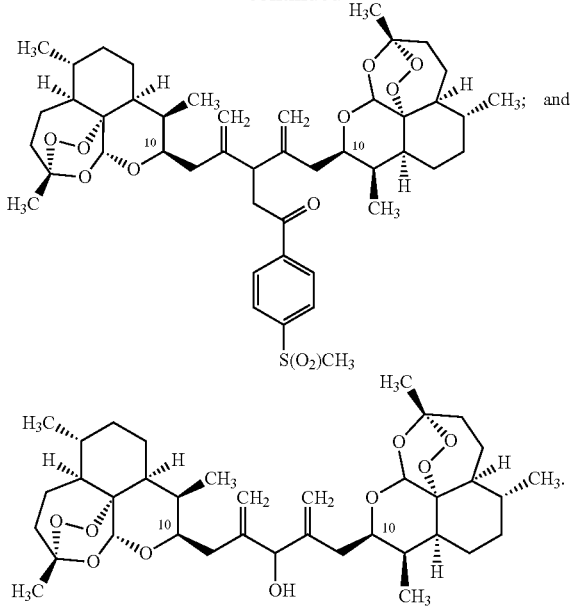

B. Chemistry

Referring once again to Scheme 4, dihydroartemisinin acetate 2d, prepared from natural trioxane 1 in near quantitative yield, Posner et al., 2003, underwent tin-promoted dimerization, Posner et al., 2003, with bis-allylic silane 10, Bigot and Breit, 2008, to form pure C-10b, C10b-trioxane dimer alcohol 11 in 59% yield. X-ray crystallography of this crystalline ester 12a confirmed the β-stereochemistry at C-10 and showed the two trioxane units to be distant from each other in the solid state. See FIG. 2. The versatile secondary alcohol functional group in dimer 11 allowed diverse benzoate ester derivatives 6 to be prepared in only one additional step in 65% to 83% yields (Scheme 4). Each of benzoate esters 12a-12c in the absence of solvent is thermally stable at the elevated temperature of 60° C. for at least 1 week and at 70° C. for at least 24 h, with less than 5% decomposition detected by $^1$H NMR spectroscopy. As C-10 non-acetals, the presently disclosed trioxane dimers are much more hydrolytically stable than the clinically used C-10 acetal trioxane drugs 2b and 2c.

C. Biology

Each trioxane dimer 12a-12c (0.90 mg) was dissolved in 0.11 mL of 7:3 Tween 80:ethanol and then diluted with 1.10 mL of distilled water for oral administration to 5-week-old C57BL/6J male mice (Jackson Laboratory) weighing about 21 g that were infected ip on day 0 with the *Plasmodium berghei*, ANKA malaria strain ($2 \times 10^7$ parasitized erythrocytes) [Chen et al., 2006]. Each of five mice in a group was treated orally 24 h post-infection with a single dose of 0.20 mL (0.20 mL/1.21 mL×0.9 mg=0.15 mg) of diluted compound solution, corresponding to a dose of 7.1 mg/kg, combined with 21 mg/kg of mefloquine hydrochloride. Both determining blood parasitemia levels, as well as monitoring the duration of animal survival compared with survival time of infected animals receiving no drug, are widely accepted measures of drug efficacy in antimalarial drug development. Three days after infection, an average of 8% blood parasitemia (microscopy after staining with Giemsa) was observed in the control (no drug) group, and by day 10 post-infection this control group showed substantial (approximately 25%) weight loss. The average survival time of the animals receiving no drug was 15.8 days post-infection. All the mice in the study receiving trioxane drug 2b or trioxane dimers 12a-12c plus mefloquine hydrochloride survived 30 days after infection and showed substantial (approximately 10-20%) weight gain. With mefloquine hydrochloride alone at a single oral dose of 21 mg/kg, one mouse died on day 30 and the remaining 4 mice on day 30 had an average of 25% parasitemia. Widely accepted indications of complete cure (i.e. 100% efficacy) are survival of animals to day 30 post-infection with no detectable malaria parasites in the animal's blood at that time. Experimental results are summarized in Table 2.

TABLE 2

Antimalarial Efficacy Using a Single Oral Dose (7.1 mg/kg) of Trioxane Combined With Mefloquine Hydrochloride (21 mg/kg) in *Plasmodium berghei*-Infected Mice.

| Trioxane | No. of mice parasite free (day 30) | % parasitemia on day 30% | suppression of parasitemia (day 3) |
|---|---|---|---|
| 2b | 4 | 1.6 (1 mouse) | >99.5 |
| 12a | 4 | 1.6 (1 mouse) | >99.5 |
| 12b | 5 | 0 | >99.5 |
| 12c | 5 | 0 | >99.5 |
| Mefloquine alone | 1 | 25 (4 mice) | 91.5 |

As provided in the data presented in Table 2, the dimeric trioxane nitrobenzoate ester 12a, at a single oral dose of only 7.1 mg/kg plus 21 mg/kg of mefloquine hydrochloride, is similar in antimalarial efficacy to trioxane drug 2b and that both dinitrobenzoate ester 12b and sulfonylbenzoate ester 12c are fully efficacious at curing the malaria-infected mice; all five mice in this 30-day surviving group were completely cured (no parasites in their blood on day 30 post-infection). All the benzoate esters 12a-12c, as well as trioxane drug 2b, caused at least 99.5% suppression of parasitemia on day 3 post-infection. The parent alcohol 5 was less efficacious than benzoate esters 12a-12c (data not shown). Neither overt toxicity nor behavioral change attributable to trioxane drug administration was observed in any of the malaria-infected animals cured by trioxane benzoate esters 12a-12c plus mefloquine hydrochloride combination.

D. Summary

In summary, three-step syntheses of dimeric trioxane benzoate esters 12 were achieved in good overall yields from the natural trioxane artemisinin 1; scale-up synthesis to kilogram quantities of these thermally and hydrolytically stable new chemical entities is expected to be straightforward. The single oral dose antimalarial efficacy of dimeric benzoate esters 12b-12c combined with mefloquine hydrochloride is at least as good as that of the popular clinically used monomeric trioxane drug 2b. Investigation of the preclinical pharmacology of dimeric trioxane benzoate esters 12a-12c will allow a fuller comparison of the chemotherapeutic value of these semi-synthetic endoperoxides versus that of the popular antimalarial trioxane drug 2b. Sagara et al., 2009; Gautam et al., 2009.

III. Trioxane Silylamides

As provided hereinabove, previous studies have reported the cure of malaria-infected mice by a single subcutaneous dose of a trioxane dimer, Posner et al., 2007; a related series of trioxane dimers curative after three oral doses, Posner et al., 2008; a trioxane dimer sulfone plus mefloquine curative after only a single oral dose, Rosenthal et al., 2009; a fluorinated amide trioxane monomer plus mefloquine curative after only a single oral dose, Woodard et al., 2009; and also a 5-carbon-linked trioxane dimer plus mefloquine curative after only a single oral dose, Moon et al., 2009. Only recently has the beneficial effect of introducing a silicon atom in place of a carbon atom in some clinically used drugs begun to be appreciated. Gately et al., 2007.

A. Representative Embodiments

Three thermally and hydrolytically stable silylamide trioxanes have been prepared from the natural trioxane artemisinin in only five simple chemical steps and in at least 56% overall yield. Two of these new chemical entities completely cured malaria-infected mice at a single oral dose of only 8 mg/kg combined with 24 mg/kg of mefloquine hydrochloride. The high efficacy of this ACT chemotherapy is considerably better than the efficacy using the popular trioxane drug artemether plus mefloquine hydrochloride.

Referring to Scheme 5, in some embodiments, the presently disclosed subject matter provides a new family of silylamide trioxane monomers 14 and a silylamide trioxane dimer 16 able to cure malaria-infected mice after only a single 8 mg/kg oral dose combined with 24 mg/kg of mefloquine hydrochloride.

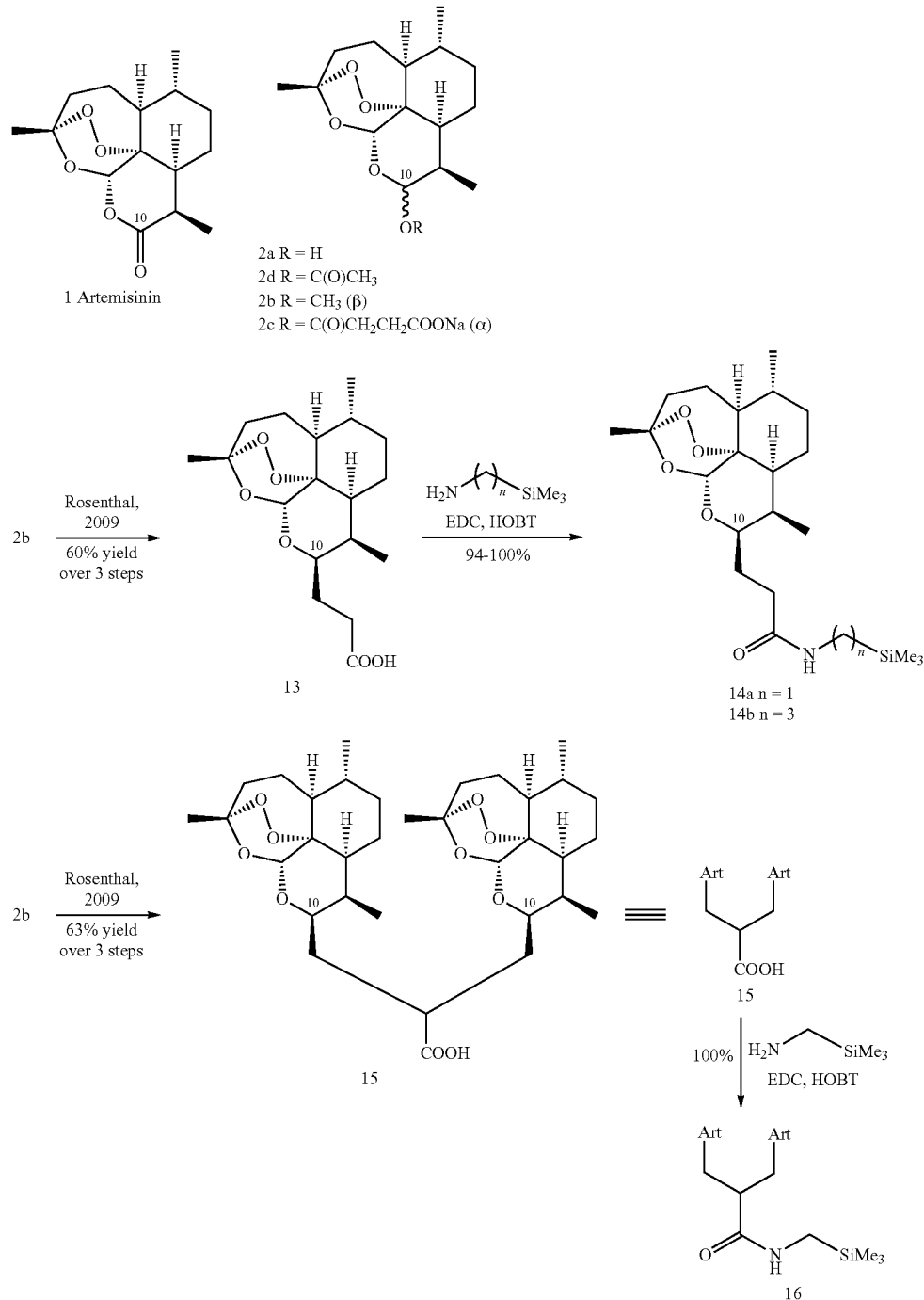

Scheme 5. Synthesis of representative trioxane silylamides.

Thus, in some embodiments, the presently disclosed subject matter provides a compound of formula (I):

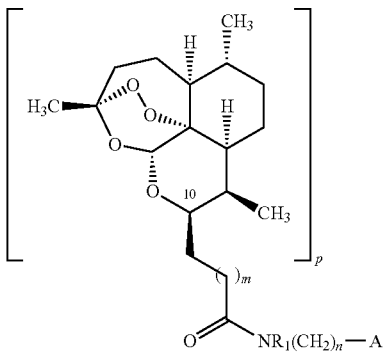

wherein:
m is an integer from 0 to 3;
n is an integer from 0 to 4;
p is an integer from 1 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
A is —Si($R_2$)$_3$, wherein each $R_2$ is independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
or an enantiomer, diastereomer, racemate or pharmaceutically acceptable salt, prodrug, or solvate thereof.

In particular embodiments, the compound of formula (I) has the following formula:

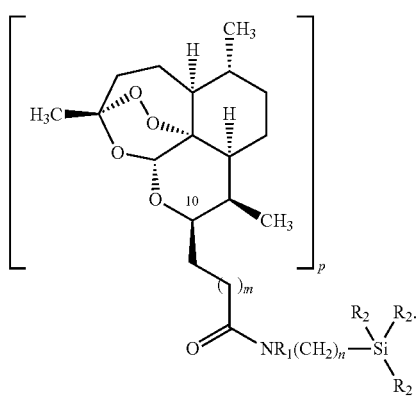

In yet more particular embodiments, the compound of formula (I) is selected from the group consisting of:

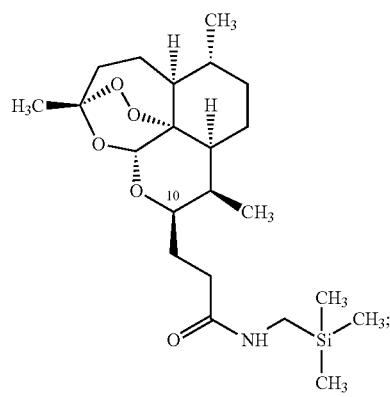

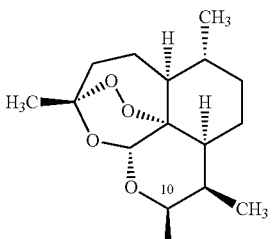

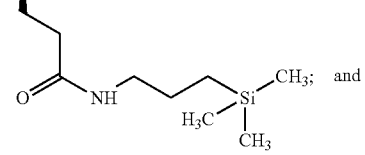

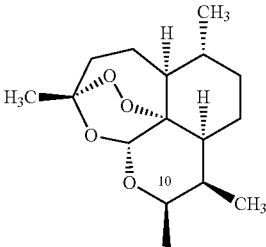

B. Chemistry

Referring once again to Scheme 5, chemical synthesis of the presently disclosed silylamide trioxane monomers 14a and 14b and silylamide trioxane dimer 16 from the natural artemisinin 1 proceeded easily on gram scale in at least 56% overall yield via dihydroartemisinin acetate 2b and then via either trioxane monomer carboxylic acid 13 or trioxane dimer carboxylic acid 15. Quantitative amide formation was achieved using commercial silylamines and standard coupling reagents. Scale up to kilogram quantities is expected to be straightforward. Silylamide trioxanes 14a, 14b, and 16 are stable in the absence of solvent for at least 7 days at 60° C. and at least 1 day at 70° C.; less than 2% decomposition was observed by proton NMR spectroscopy. Because these silylamides are C-10 non-acetal trioxanes, they are more hydrolytically stable than the clinically used C-10 acetal trioxane drugs 2c and 2d.

C. Biology

Each trioxane silylamide 14a, 14b, and 16 (0.90 mg) was dissolved in 0.11 mL of 7:3 Tween 80:ethanol and then diluted with 1.10 mL of water for oral administration to 5-week old C57BU6J male mice (from the Jackson Laboratory) weighing 18-19 grams that were infected intraperitoneally on day 0 with the *Plasmodium berghei*, ANKA strain ($2 \times 10^7$ parasitized erythrocytes). Woodard et al., 2009. Each of 3 mice in a group was treated orally 24 hours post-infection with a single dose of 0.20 mL (0.20 mL/1.21 mL×0.9 mg=0.15 mg) of diluted compound solution, corresponding to a dose of 8 mg/kg, combined with 24 mg/kg of mefloquine hydrochloride. Determining blood parasitemia levels, as well as monitoring the duration of animal survival compared to survival time of animals receiving no drug, are both widely accepted as measures of a drug's efficacy in antimalarial drug development. Three days after infection, an average of 7% blood parasitemia was observed in the control (infected but no drug) group. Animals infected but receiving no drug died on an average of 15 days post-infection. A widely accepted yardstick of cure (i.e., 100% efficacy) is survival of animals to at least day 30 post-infection, with no detectable malaria parasites in the animal's blood at that time. Average survival results through day 57 (when the experiment was stopped) are summarized in Table 3.

TABLE 3

Antimalarial Efficacy Using a Single Oral Dose of Trioxane (8 mg/kg) Combined with Mefloquine Hydrochloride (24 mg/kg) in *Plasmodium berghei*-infected Mice.

| Trioxane | Average Survival (days) after Infection | % Suppression of Parasitemia (on day 3 post-infection) |
|---|---|---|
| 2c | 23 | >99.5 |
| 14a | >57 | >99.5 |
| 14b | 44[a] | >99.5 |
| 16 | >57 | >99.5 |

[a]One mouse died on day 17; the other two mice in this group showed no parasitemia on day 57.

As provided in Table 3, both silylamides 14a and 16 administered as a single oral dose of 8 mg/kg plus mefloquine hydrochloride (24 mg/kg) cured the malaria-infected mice; on day 57 (when the experiment was terminated), no parasites were detected in the blood of the surviving mice. At a single oral dose of 22 mg/kg, mefloquine hydrochloride alone was not curative. In an ACT control experiment, the popular trioxane drug artemether (2c) combined with mefloquine hydrochloride prolonged mouse average survival until only day 23 (Table 3). Neither overt toxicity nor behavioral change attributable to trioxane drug administration was observed in any of the malaria-infected animals cured by trioxane 14a or 16 plus mefloquine hydrochloride combination. By the end of the experiment, all the mice receiving the silylamides 14a and 16 had gained as much weight (8-10 g) as had the mice in an uninfected control group: this weight gain result is a strong indication of the apparent safety of these silylamides under conditions in which they are curative.

D. Summary

In summary, a single-digit oral dose of trioxane monomer silylamide 14a or of trioxane dimer silylamide 16, combined with mefloquine hydrochloride, is considerably more antimalarially efficacious than the popular ACT trioxane drug artemether (2c) combined with mefloquine hydrochloride. WHO 2006; Sagara et al., 2009; Gautam et al., 2009; Arinaitwe et al., 2009; Eastman and Fidock, 2009. Complete cure of malaria-infected mice was achieved with silylamides 14a and 16, which appear to be safe at the curative dose.

IV. Trioxane Dimer Orthoesters

In some embodiments, the presently disclosed subject matter provides trioxane dimer orthoesters. Referring now to Scheme 6, representative trioxane dimer orthoesters can be prepared from a presently disclosed 5-carbon-linked, C-10 trioxane dimer alcohol, e.g., compound 11 of scheme 4.

Scheme 6. Synthesis of representative trioxane dimer orthoesters.

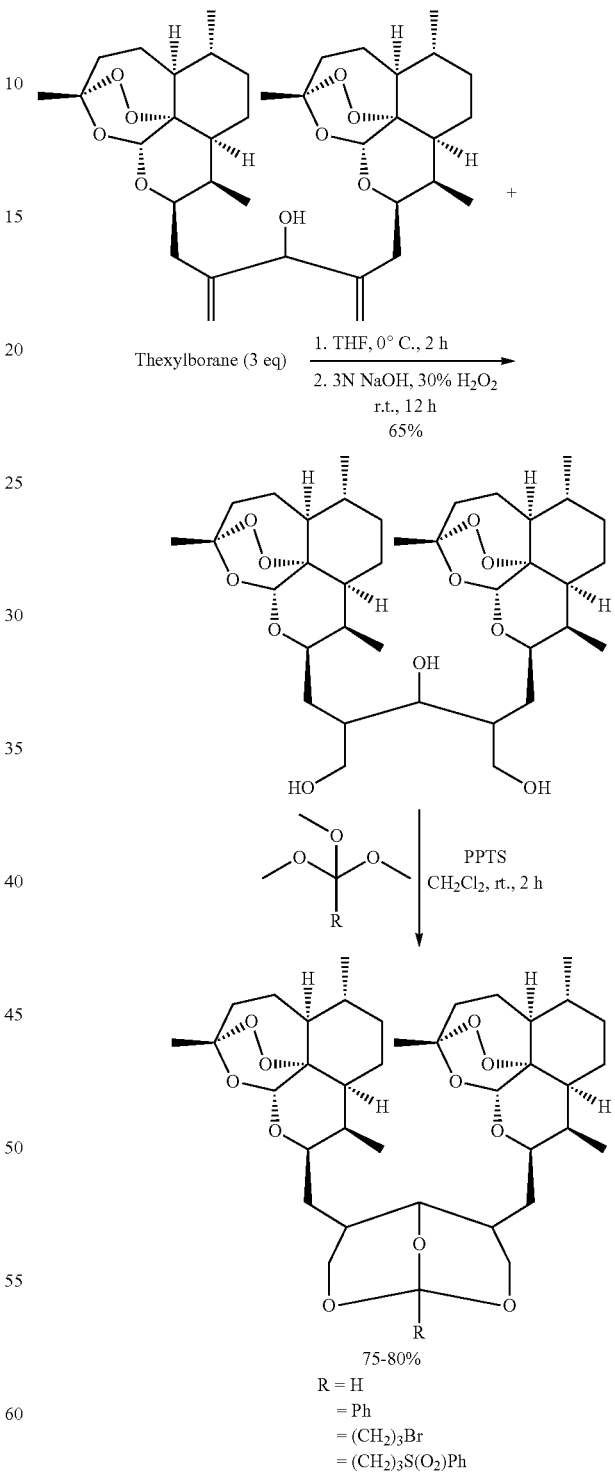

More particularly, in some embodiments, the presently disclosed subject matter provides a compound of formula (III):

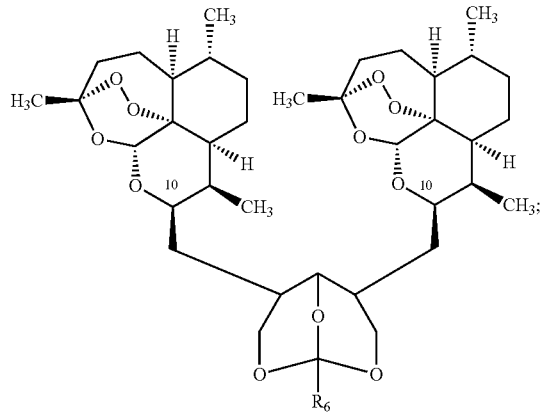

(III)

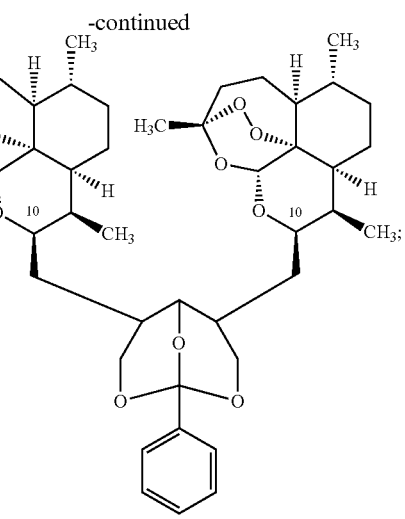
-continued wherein:

R$_6$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, substituted or unsubstituted heteroarylalkyl, —(CH$_2$)$_t$—X, and —(CH$_2$)$_s$S(O$_2$)Ar$_1$;

wherein s and t are each independently an integer from 1 to 8, X is halogen, and Ar$_1$ is selected from the group consisting of substituted or unsubstituted aryl or substituted and unsubstituted heteroaryl;

or an enantiomer, diastereomer, racemate or pharmaceutically acceptable salt, prodrug, or solvate thereof.

In particular embodiments, R$_6$ is selected from the group consisting of hydrogen, aryl or substituted aryl, —(CH$_2$)$_r$X, and —(CH$_2$)$_r$S(O$_2$)Ar$_1$. In such embodiments, the compound of formula (III) can include a structure selected from the group consisting of:

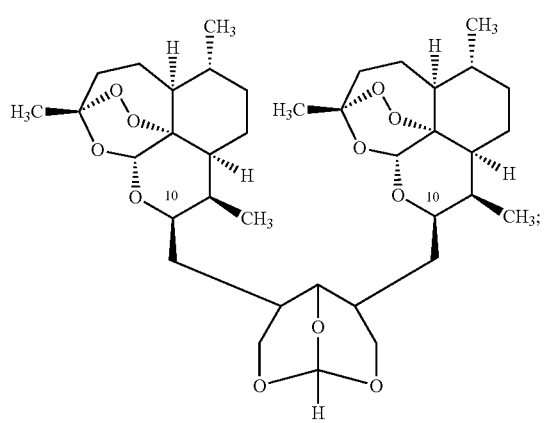

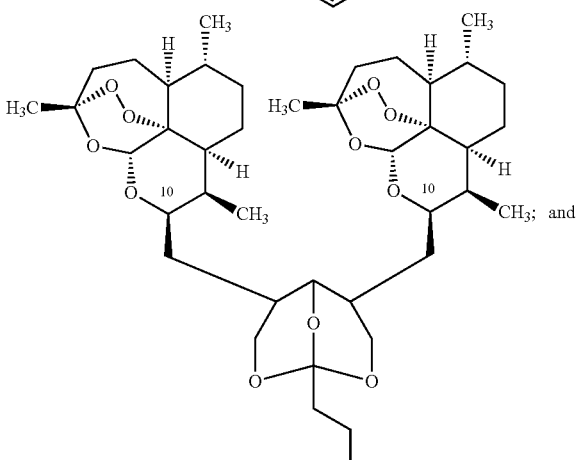

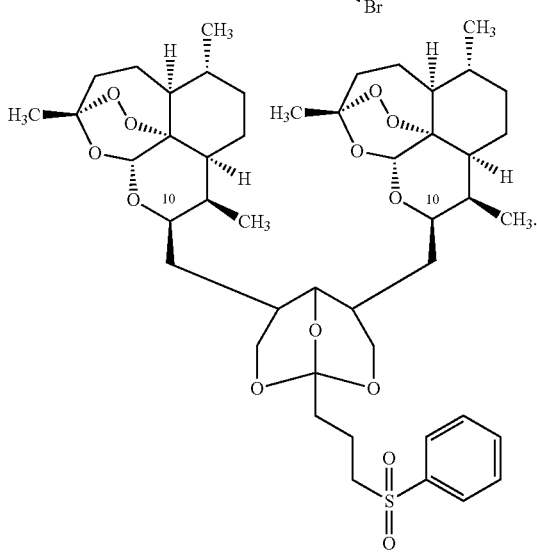

V. Methods of Treatment

In some embodiments, the presently disclosed monomeric and dimeric trioxane fluoroaryl amides; 5-carbon-linked, C-10 non-acetal trioxane dimer esters; trioxane silylamides, and trioxane dimer orthoesters can be used for treating subjects infected with malaria or other parasitic infectious diseases including, but not limited to, toxoplasmic infection; subjects afflicted with psychiatric conditions associated with toxoplasmic infection; and subjects afflicted with cancer.

A. Methods of Treating Subject Infected with Malaria

Each year approximately 200-300 million people experience a malarial illness and over 1 million individuals die. In patients with severe and complicated disease, the mortality rate is between 20 and 50%. *Plasmodium* is the genus of protozoan parasites that is responsible for all cases of human malaria and *Plasmodium falciparum* is the species of parasite that is responsible for the vast majority of fatal malaria infections. Malaria has traditionally been treated with quinolines, such as chloroquine, quinine, mefloquine, and primaquine, and with antifolates, such as sulfadoxine-pyrimethamine. Unfortunately, most *P. falciparum* strains have now become resistant to chloroquine, and some, such as those in Southeast Asia, also have developed resistance to mefloquine and halofantrine; multidrug resistance also is developing in Africa.

The endoperoxides are a promising class of antimalarial drugs that may meet the dual challenges posed by drug-resistant parasites and the rapid progression of malarial illness. As discussed hereinabove, the first generation endoperoxides include natural artemisinin and several synthetic derivatives. Artemisinin has been used successfully to treat malaria patients throughout the world, including those infected with both chloroquine-sensitive and chloroquine-resistant strains of *P. falciparum*.

Although artemisinin is effective at suppressing the parasitemias of *P. vivax* and *P. falciparum*, the problems encountered with recrudescence, and the compound's insolubility in water, led scientists to modify artemisinin chemically, a difficult task because of the chemical reactivity of the peroxide linkage, which is believed to be an essential moiety for antimalarial activity. In some embodiments, the presently disclosed subject matter provides a new series of monomeric and dimeric trioxane fluoroaryl amides; 5-carbon-linked, C-10 non-acetal trioxane dimer esters; trioxane silylamides; and trioxane dimer orthoesters useful for treating subjects infected with malaria.

Accordingly, the presently disclosed subject matter provides a method of treating a subject infected with malaria, the method comprising administering to a subject in need of treatment thereof, a compound of formula (I), formula (II), or formula (III) as disclosed herein. In some embodiments, the method further comprises administering to the subject a quinoline anti-malarial drug concurrently or sequentially with a compound of formula (I), formula (II), or formula (III). In particular embodiments, the quinoline anti-malarial drug is selected from the group consisting of chloroquine, quinine, mefloquine, and primaquine. In more particular embodiments, the anti-malarial drug is mefloquine.

B. Methods of Treating Other Parasitic Infectious Diseases

In some embodiments, the presently disclosed monomeric and dimeric trioxanes are useful for preventing, treating and controlling infections, including but not limited to toxoplasmic infection, and psychiatric conditions associated with toxoplasmic infection. *Toxoplasma gondii* (*T. gondii*) is an apicomplexan protozoan of world-wide medical importance. Humans are infected by *T. gondii* through contact with feces from infected cats, by the consumption of undercooked meat from infected animals, or by transmission from infected mother to fetus. This parasite can cause systemic infection and widespread organ damage in immunocompromised individuals and neonates. Infection of immunocompetent adults can result in fever and adenopathy. Tenter et al., 2000. Serological studies indicate that *T. gondii* could be associated with chronic neuropsychiatric diseases or behavioral abnormalities in some populations. Bachmann et al., 2005; Yolken et al., 2001.

Available medications for the prevention and treatment of *toxoplasma* infection show limited efficacy and have substantial side effects. Georgiev 1994. Published studies have indicated that the naturally occurring 1,2,4-trioxane artemisinin and artemisinin derivatives, such as artemether, originally developed for the treatment of malaria, have the ability to inhibit *toxoplasma* replication in vitro. Berens et al., 1998; Chang et al., 1989; Holfels et al., 1994; Ou-Yang et al., 1990.

While these trioxanes have a number of advantages in terms of rapid action and low levels of toxicity, they are limited in terms of absorption, bioavailability, and short half-life (i.e., easy hydrolysis into toxic dihydroartemisinin). Lin et al., 1987; O'Neill and Posner, 2004. Thus, what is needed are improved derivatives of artemisinin having not only rapid action and low levels of toxicity, but also better absorption, bioavailability, and longer half-lives for inhibiting the replication of *T. gondii*. Selected derivatives of artemisinin exhibiting in vitro efficacy against *T. gondii* are disclosed in published PCT patent application no. WO2008/127381 to Brando et al., which is incorporated herein by reference in its entirety. The artemisinin derivatives disclosed in WO2008/127381 also have been shown to inhibit the replication of chloroquine-sensitive *Plasmodium falciparum*.

Accordingly, in some embodiments, the presently disclosed subject matter provides methods of using the presently disclosed monomeric and dimeric trioxane compounds and compositions for preventing, controlling or treating infectious diseases, including but not limited to, parasitic infectious diseases, such as *T. gondii* infection, trypanosome parasite infection, plasmodia parasite infection, and *Cryptosporidium* parasite infection.

Further, the evidence linking infection with *T. gondii* to the etiology of schizophrenia is well known. Torrey et al., 2007. Epidemiologic studies have indicated that infectious agents may contribute to some cases of schizophrenia. In animals, infection with *T. gondii* can alter behavior and neurotransmitter function. In humans, acute infection with *T. gondii* can produce psychotic symptoms similar to those displayed by persons with schizophrenia. Since 1953, a total of 19 studies of *T. gondii* antibodies in persons with schizophrenia and other severe psychiatric disorders and in controls have been reported; 18 reported a higher percentage of antibodies in the affected persons; in 11 studies the difference was statistically significant. Two other studies found that exposure to cats in childhood was a risk factor for the development of schizophrenia. Some medications used to treat schizophrenia inhibit the replication of *T. gondii* in cell culture. Jones-Brando et al., 2003. Establishing the role of *T. gondii* in the etiopathogenesis of schizophrenia may lead to new medications for its prevention and treatment.

Schizophrenia is a pervasive neuropsychiatric disease of uncertain cause that affects approximately 1% of the adult population in the United States and Europe. An increased occurrence of schizophrenia in family members of affected persons suggests that genetic factors play a role in its etiology, and some candidate predisposing genes have been identified. Environmental factors also are important. Epidemiologic studies, for example, have established that winter-spring birth, urban birth, and perinatal and postnatal infection are all risk factors for the disease developing in later life. These studies have rekindled an interest in the role of infectious agents in schizophrenia, a concept first proposed in 1896.

*T. gondii* is an intracellular parasite in the phylum Apicomplexa. Its life cycle can be completed only in cats and other felids, which are the definitive hosts. *T. gondii*, however, also infects a wide variety of intermediate hosts, including humans. In many mammals, *T. gondii* is known to be an important cause of abortions and stillbirths and to selectively infect muscle and brain tissue. A variety of neurologic symptoms, including incoordination, tremors, head-shaking, and seizures, have been described in sheep, pigs, cattle, rabbits, and monkeys infected with *T. gondii*. Humans may become infected by contact with cat feces or by eating undercooked meat. The importance of these modes of transmission may vary in different populations. Individual response to *Toxoplasma* infection is determined by immune status, timing of infection, and the genetic composition of the host and the organism.

*Toxoplasma* organisms have also been shown to impair learning and memory in mice and to produce behavioral changes in both mice and rats. Of special interest are studies showing that *Toxoplasma*-infected rats become less neophobic, leading to the diminution of their natural aversion to the odor of cats. These behavioral changes increase the chances that the rat will be eaten by a cat, thus enabling *Toxoplasma* to complete its life cycle, an example of evolutionarily driven manipulation of host behavior by the parasite.

In humans, *toxoplasma* is an important cause of abortions and stillbirths after primary infection in pregnant women. The organism also can cross the placenta and infect the fetus. The symptoms of congenital toxoplasmosis include abnormal changes in head size (hydrocephaly or microcephaly), intracranial calcifications, deafness, seizures, cerebral palsy, damage to the retina, and mental retardation. Some sequelae of congenital toxoplasmosis are not apparent at birth and may not become apparent until the second or third decade of life. Hydrocephalus, increased ventricular size, and cognitive impairment also have been noted in some persons with schizophrenia and other forms of psychosis.

Some cases of acute toxoplasmosis in adults are associated with psychiatric symptoms, such as delusions and hallucinations. Schizophrenia was first diagnosed in these patients, but later neurologic symptoms developed, which led to the correct diagnosis of *Toxoplasma* encephalitis.

Chlorpromazine (THORAZINE®) is the first antipsychotic medication used for schizophrenia, which was soon followed by other medications, such as haloperidol (HALDOL®), fluphenazine (PROLIXIN®), thiothixene (NAVANE®), trifluoperazine (STELAZINE®), perphenazine (TRILAFON®), and thioridazine (MELLARIL®). These medications have become known as "neuroleptics" because, although effective in treating positive symptoms (i.e., acute symptoms such as hallucinations, delusions, thought disorder, loose associations, ambivalence, or emotional lability), cause side effects, many of which affect the neurologic (nervous) system.

A new class of antipsychotics (atypical antipsychotics) was introduced after 1989. At clinically effective doses, no (or very few) of these neurological side effects, which often affect the extrapyramidal nerve tracts (which control such things as muscular rigidity, painful spasms, restlessness, or tremors) are observed. The first of the new class, clozapine (CLOZARIL®) is the only agent that has been shown to be effective where other antipsychotics have failed. Its use is not associated with extrapyramidal side effects, but it does produce other side effects, including possible decrease in the number of white cells, so the blood needs to be monitored every week during the first 6 months of treatment and then every 2 weeks to catch this side effect early if it occurs. Other atypical antipsychotics include risperidone (RISPERDAL®), olanzapine (ZYPREXA®), quetiapine (SEROQUEL®), ziprasidone (GEODON®), and aripiprazole (ABILITY®). The use of these medications has allowed successful treatment and release back to their homes and the community for many people suffering from schizophrenia.

Accordingly, in some embodiments, the presently disclosed subject matter provides a method for treating psychiatric disorders associated with *toxoplasma* infection including, but not limited to, schizophrenia, using the presently disclosed monomeric and dimeric trioxane compounds of formula (I), formula (II), or formula (III) and compositions thereof alone or in combination with one or more antipsychotic drugs including, but not limited to, chlorpromazine (THORAZINE®), haloperidol (HALDOL®), fluphenazine (PROLIXIN®), thiothixene (NAVANE®), trifluoperazine (STELAZINE®), perphenazine (TRILAFON®), and thioridazine (MELLARIL®), clozapine (CLOZARIL®), risperidone (RISPERDAL®), olanzapine (ZYPREXA®), quetiapine (SEROQUEL®), ziprasidone (GEODON®), and aripiprazole (ABILIFY®).

C. Methods of Treating Cancer

Since the isolation of artemisinin, there has been a concerted effort by investigators to study other therapeutic applications of artemisinin and its derivatives. The National Institutes of Health reported that artemisinin is inactive against P388 leukemia (NCI Report on NSC 369397, tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian, renal, prostate and breast cancers, further confirm that artemisinin displays modest anticancer activity.

While artemisinin and its related derivatives demonstrate zero to slight antiproliferative and antitumor activity, it has been discovered that a class of artemisinin dimer compounds exhibits antiproliferative and antitumor activities that are, in vitro, equivalent to or greater than known antiproliferative and antitumor agents (U.S. Pat. No. 5,677,468 also incorporated herein by reference in its entirety for all purposes). Unfortunately, while the in vitro results of these artemisinin compounds are encouraging, these compounds do not appear to have as significant antitumor activity on the treatment of tumor cells in mice.

There is still a need, therefore, to develop stable artemisinin derivatives and structural analogs thereof having antimalarial, anticancer, antiproliferative, and antitumor activities that are equivalent to or greater than those of known antimalarial, anticancer, antiproliferative and antitumor agents, respectively. For example, selected artemisinin-related dimers, e.g., trioxane dimer sulfur compounds, having anticancer activity have been disclosed in international PCT patent application publication no. WO2010/009428, to Posner and Rosenthal, which is incorporated herein by reference in its entirety. Other artemisinin analogs, including trioxane dimers have been shown to exhibit anti-cancer activity. See, e.g., U.S. patent application publication nos. US2009/0291923, to Posner et al., published Nov. 26, 2009; US2006/0142377 to Posner et al., published Jun. 29, 2006; and US2002/0055528 to Posner et al., published May 9, 2002, each of which is incorporated herein by reference in its entirety.

Accordingly, in some embodiments, the presently disclosed subject matter provides a method for treating cancer in a subject in need of such treatment, by administering to the subject a therapeutically effective amount of the presently disclosed monomeric and dimeric trioxane compounds of formula (I), formula (II), or formula (III). The cancer can include leukemia, non-small cell lung cancer, colon cancer, central nervous system cancer, melanoma cancer, ovarian cancer, renal cancer, prostate cancer, and breast cancer.

VI. Pharmaceutical Compositions and Administration

In another aspect, the present disclosure provides a pharmaceutical composition including one or more monomeric and dimeric trioxane compounds of formula (I), formula (II), and/or formula (III) alone or in combination with one or more additional therapeutic agents in admixture with a pharmaceutically acceptable excipient. One of skill in the art will recognize that the pharmaceutical compositions include the pharmaceutically acceptable salts of the compounds described above.

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

The compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP:povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this disclosure. For example, chemotherapeutic agents or other antiproliferative agents may be combined with the inhibitors of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents in which the disclosed trioxane sulfur dimer compounds may also be combined with include, without limitation, anti-inflammatory agents such as corticosteroids, TNF blockers, IL-I RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors, such as acetylcholinesterase inhibitors, MAO inhibitors, interferons, anti-convulsants, ion channel blockers, riluzole, and antiparkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders, such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

VII. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formulae I-X are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted, for example, with fluorine at one or more positions).

Where substituent groups or linking groups are specified by their conventional chemical formulae, written from left to right, they equally encompass the chemically identical substituents that would result from writing the structure from right to left, e.g., —$CH_2O$— is equivalent to —$OCH_2$—; —$C(=O)O$— is equivalent to —$OC(=O)$—; —$OC(=O)NR$— is equivalent to —$NRC(=O)O$—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, methoxy, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons). In particular embodiments, the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to, alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

As described above, heteroalkyl groups, as used herein, include those groups that are attached to the remainder of the molecule through a heteroatom, such as —C(O)R', —C(O)NR', —NR'R", —OR', —SR, and/or —SO$_2$R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —CH$_2$CH$_2$CH$_2$CH$_2$—, —CH$_2$CH=CHCH$_2$—, —CH$_2$C≡CCH$_2$—, —CH$_2$CH$_2$CH(CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

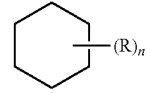

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

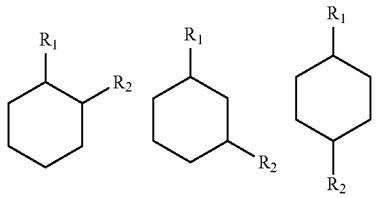

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ~~~~~~ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =NR—OR', —NR'R'', —SR', -halogen, —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R'')=NR''', —S(O)R', —S(O)$_2$R', —S(O)$_2$NR'R'', —NRSO$_2$R', —CN and —NO$_2$ in a number ranging from zero to (2 m'+1), where m' is the total number of carbon atoms in such groups. R', R'', R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 4-, 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R'', —SR', -halogen, —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R''R''')=NR'''', —NR—C(NR'R'')=NR'''—S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxo, and fluoro (C$_1$-C$_4$)alkyl, in a number ranging from zero to the total number of open valences on aromatic ring system; and where R', R'', R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R'', R''' and R'''' groups when more than one of these groups is present.

Two of the substituents on adjacent atoms of aryl or heteroaryl ring may optionally form a ring of the formula -T-C (O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'' and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxy, n-hexoxy, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an amide group of the formula —CONH$_2$. "Alkylcarbamoyl" refers to a R'RN—CO— group wherein one of R and R' is hydrogen and the other of R and R' is alkyl and/or substituted alkyl as previously described. "Dialkylcarbamoyl" refers to a R'RN—CO— group wherein each of R and R' is independently alkyl and/or substituted alkyl as previously described.

The term carbonyldioxyl, as used herein, refers to a carbonate group of the formula —O—CO—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R'', wherein R' and R'' are each independently selected from the group consisting of alkyl groups. The term trialkylamino refers to a group having the structure —NR'R''R''', wherein R', R'', and R''' are each independently selected from the group consisting of alkyl groups. Additionally, R', R'', and/or R''' taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino.

The amino group is —NR'R'', wherein R' and R'' are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —(C=O)— group.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

The term ureido refers to a urea group of the formula —NH—CO—NH$_2$.

Unless otherwise explicitly defined, a "substituent group," as used herein, includes a functional group selected from one or more of the following moieties, which are defined herein:

(A) -OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "lower substituent" or "lower substituent group," as used herein means a group selected from all of the substituents described hereinabove for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

Throughout the specification and claims, a given chemical formula or name shall encompass all tautomers, congeners, and optical- and stereoisomers, as well as racemic mixtures where such isomers and mixtures exist.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)— or (S)— or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

As used herein the term "monomer" refers to a molecule that can undergo polymerization, thereby contributing constitutional units to the essential structure of a macromolecule or polymer.

A "polymer" is a molecule of high relative molecule mass, the structure of which essentially comprises the multiple repetition of unit derived from molecules of low relative molecular mass, i.e., a monomer.

As used herein, an "oligomer" includes a few monomer units, for example, in contrast to a polymer that potentially can comprise an unlimited number of monomers. Dimers, trimers, and tetramers are non-limiting examples of oligomers.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The term "pharmaceutically acceptable salts" is meant to include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

The term "protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(O)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

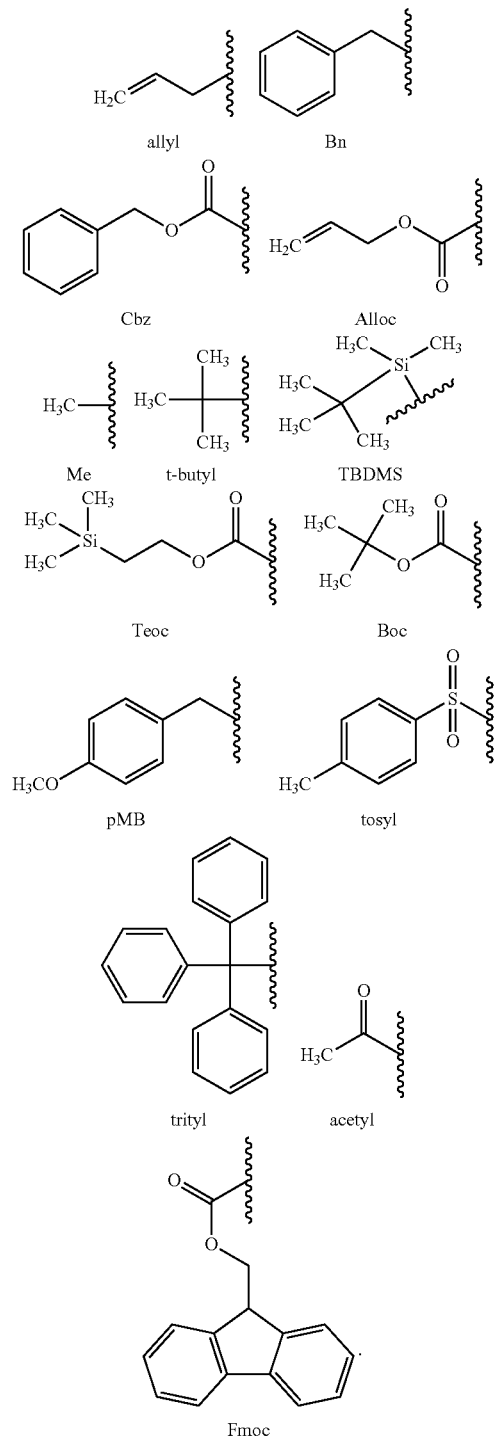

The subject treated by the presently disclosed methods in their many embodiments is desirably a human subject, although it is to be understood that the methods described herein are effective with respect to all vertebrate species, which are intended to be included in the term "subject."

Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis of Monomeric and Dimeric Trioxane Fluoroaryl Amides

Experimental

High-pressure liquid chromatography (HPLC) was performed on a Rainin HPLX system equipped with two 25 mL pump heads and a Rainin Dynamax UV-C dual-beam variable wavelength detector set at 254 using a Phenomenex Luna 5µ C18 250 mm×10 mm column. The purity of analogs 3, 4a, and 4b was ≥98% based on HPLC analysis.

Synthesis of Trioxane Dimer Fluoroaryl Amide (3)

Referring now to Scheme 2, to a solution of acid 6, Posner et al., 2003, (600 mg, 0.967 mmol) in $CH_2Cl_2$ (10 mL) were added N-(3-dimethylaminopropyl)-N'-ethylcarbodiimide hydrochloride (222 mg, 1.16 mmol) and 1-hydroxybenzotriazole (157 mg, 1.16 mmol) and it was stirred for 1 h at rt. To the reaction were added 4-fluorobenzylamine (0.33 mL, 2.9 mmol), and the solution was stirred for 5 h. It was quenched with water (3 mL). Layers were separated and the aqueous layer was extracted with EtOAc (2×4 mL). The combined organic solution was dried ($MgSO_4$) and concentrated. The residue was purified by flash column chromatography (elution with EtOAc:hexanes=1:3) to provide 3 (651 mg, 93%) as a white solid: $[\alpha]_D^{24}$=+82.1 (c=1.55, $CHCl_3$); mp=110° C. IR (thin film) 3312, 2939, 1669, 1510, 1377, 1221, 1052, 1012, 735 cm$^{-1}$. $^1$H NMR (400 MHz, $CDCl_3$) δ 7.32 (m, 2H), 6.97 (m, 2H), 6.23 (t, J=5.6 Hz, 1H), 5.27 (s, 1H), 5.20 (s, 1H), 4.41 (s, 1H), 4.39 (s, 1H), 4.09 (m, 2H), 2.76 (dq, J=13.2, 7.2 Hz, 1H), 2.66 (dq, J=13.6, 6.4 Hz, 1H), 2.54 (octet, J=4.0 Hz, 1H), 2.31 (m, 2H), 2.18 (m, 1H), 2.01-1.95 (m, 3H), 1.92-1.18 (m, 24H including s at 1.35 and 1.26), 0.98-0.79 (m, 14H including d at 0.95 with J=5.6 Hz, 0.93 with J=6.0 Hz, 0.85 with J=7.6 Hz, and 0.82 with J=7.2 Hz). $^{13}$C NMR (100 MHz, $CDCl_3$) δ 175.8, 160.8, 134.3, 129.8, 129.7, 115.3, 115.1, 103.4, 102.9, 100.8, 88.6, 88.4, 81.2, 81.1, 76.4, 73.7, 52.5, 52.4, 44.7, 44.5, 44.3, 43.3, 37.4, 37.2, 36.5, 34.5, 33.3, 32.9, 30.2, 29.9, 26.2, 26.0, 24.9, 24.8, 24.6, 24.5, 20.2, 13.5, 13.0. $^{19}$F NMR (282 MHz, $CDCl_3$) δ −115.7. HRMS (FAB) calculated for $C_{41}H_{59}FNO_9[(M+H)^+$ ] 728.4174. Found 728.4177.

Synthesis of Trioxane Monomer Fluoroaryl Amide (4a)

Referring now to Scheme 3, into a flame-dried 5 mL RBF was charged acid 8, Jung et al., 2003, (75 mg, 0.22 mmol), N-(3-dimethylaminopropyl)-N'-ethylcarbodiimide hydrochloride (67 mg, 0.35 mmol), and 1-hydroxybenzotriazole (35 mg, 0.26 mmol). Dichloromethane (2.5 mL) was then added, and the mixture was stirred for an hour, at which time 4-fluorobenzylamine (95 μL, 0.84 mmol) was added by syringe. The reaction was allowed to stir at room temperature for 3 h. It was then quenched with 1 N HCl, extracted with dichloromethane (3×5 mL), washed with aqueous NaHCO$_3$ and brine, dried over magnesium sulfate, and evaporated. The crude product was purified by preparative thin layer chromatography (silica gel, 100% diethyl ether) to afford 4a as an amorphous, white solid (69 mg, 0.15 mmol, 70%). IR (thin film) 3321, 2947, 2875, 1648, 1546, 1510, 1453, 1378, 1223, 1127, 1095, 1052, 1011, 940, 879, 822, 756 cm$^{-1}$. $^1$H NMR (400 MHz, CDCl$_3$) δ 7.25 (m, 2H), 7.00 (m, 2H), 6.08 (br. s, 1H), 5.27 (s, 1H), 4.40 (m, 2H), 4.09 (m, 1H), 2.69 (m, 1H), 2.46 (m, 1H), 2.33 (m, 2H), 2.04-1.77 (m, 5H), 1.64-1.55 (m, 2H), 1.48-1.20 (m, 7H, including singlet at 1.36), 0.99-0.92 (m, 4H), 0.85 (d, 3H, J=6.0 Hz). $^{13}$C NMR (100 MHz, CDCl$_3$) δ 172.97, 163.40, 160.96, 134.27, 129.54, 115.41, 103.28, 88.91, 81.14, 75.75, 52.44, 44.45, 43.01, 37.43, 36.58, 34.64, 34.48, 30.22, 26.11, 25.15, 24.89, 24.68, 20.12, 13.00; $[α]_D^{22}$=+72 (c=0.97, CHCl$_3$). HRMS (FAB) m/z calcd for C$_{25}$H$_{34}$FNO$_5$Na (M+Na)$^+$ 470.2313. Found 470.2300.

Synthesis of Trioxane Monomer Fluoroanilide (4b)

Referring again to Scheme 3, into a flame-dried 5 mL RBF was charged carboxylic acid 8, Jung et al., 2003, (55 mg, 0.16 mmol), N-(3-dimethylaminopropyl)-N'-ethylcarbodiimide hydrochloride (50 mg, 0.26 mmol), and 1-hydroxybenzotriazole (30 mg, 0.19 mmol). Dichloromethane (2.5 mL) was then added and the mixture was stirred for an hour, at which time 4-fluoroaniline (60 μL, 0.61 mmol) was added by syringe. The reaction was allowed to stir at room temperature for 3 h. It was then quenched with 1 N HCl, extracted with dichloromethane (3×5 mL), washed with aqueous NaHCO$_3$ and brine, dried over magnesium sulfate, and evaporated. The crude product was purified by flash column chromatography (silica gel, 30% ethyl acetate/hexanes) to afford 4b (artefanilide) as an amorphous, white solid (51 mg, 0.12 mmol, 75%). IR (thin film) 3313, 2939, 2874, 1663, 1614, 1543, 1509, 1451, 1406, 1377, 1212, 1124, 1091, 1055, 1012, 876, 835, 754 cm$^{-1}$. $^1$H NMR (400 MHz, CDCl$_3$) δ 8.07 (br. s, 1H), 7.50 (m, 2H), 6.96 (m, 2H), 5.34 (s, 1H), 4.14 (m, 1H), 2.73 (m, 1H), 2.60 (m, 1H), 2.46 (m, 1H), 2.31 (m, 1H), 2.02-1.78 (m, 5H), 1.65-1.55 (m, 2H), 1.47-1.20 (m, 7H, including singlet at 1.35), 0.97-0.93 (m, 4H), 0.87 (d, 3H, J=7.6 Hz). $^{13}$C NMR (100 MHz, CDCl$_3$) δ 171.33, 157.89, 134.17, 121.63, 115.33, 103.42, 88.79, 81.08, 76.12, 52.30, 44.31, 37.34, 36.42, 35.62, 34.32, 30.85, 30.13, 25.98, 24.82, 24.55, 20.09, 13.04; $[α]_D^{22}$=+60 (c=0.47, CHCl$_3$). HRMS (FAB) m/z calcd for C$_{24}$H$_{33}$FNO$_5$ (M+H)$^+$ 434.2343. Found 434.2335.

Synthesis of LW-ART-EtC(O)—NH-2-pyrid-5-F

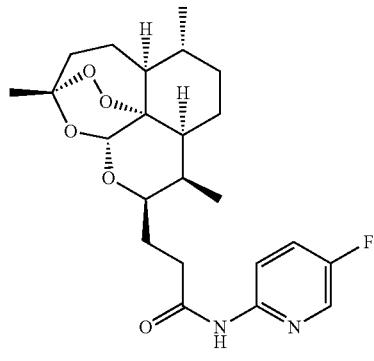

LW-ART-EtC(O)-NH-2-pyrid-5-F

A flame dried 5 mL round bottom flask was charged with carboxylic acid monomer (40 mg, 0.12 mmol) and anhydrous THF (5 mL). The flask was cooled to −40° C. and N-methyl-morpholine (13 μL, 0.12 mmol) and isobutyl chloroformate (16 μL, 0.12 mmol) were added via plastic syringe. The reaction stirred for two hours, at which time commercial 2-amino-5-fluoropyridine (13 mg, 0.12 mmol) was added. The reaction was allowed to warm to room temperature and stirred for 72 hours. The THF was then evaporated and the reaction was redissolved in dichloromethane, washed successively with sodium bicarbonate, water and brine, dried over magnesium sulfate and evaporated. The crude product was purified by preparative thin layer chromatography (silica gel, 30% EtOAc/Hexanes) to afford LW-ART-EtC(O)—NH-2-pyrid-5-F (immediately hereinabove) as an amorphous, white solid (23 mg, 0.053 mmol, 44%): IR (thin film) 3266, 2942, 2876, 1696, 1595, 1527, 1472, 1391, 1295, 1266, 1230, 1177, 1122, 1092, 1056, 1011, 946, 910 cm$^{-1}$; $^1$H NMR (400 MHz, CDCl$_3$) δ 8.57 (br. s, 1H), 8.23-8.12 (m, 2H), 7.42 (m, 1H), 5.30 (s, 1H), 4.15 (m, 1H), 2.73-2.64 (m, 2H), 2.50 (m, 1H), 2.30 (m, 1H), 2.02-1.77 (m, 5H), 1.66-1.56 (m, 2H), 1.49-1.19 (m, 7H, including singlet at 1.33), 0.94 (m, 4H), 0.86 (d, 3H, J=7.6 Hz); $^{13}$C NMR (100 MHz, CDCl$_3$) δ 171.61, 147.74, 136.05, 125.63, 115.08, 103.26, 88.90, 81.13, 75.07, 52.33, 44.33, 37.40, 36.52, 35.39, 34.43, 30.17, 26.03, 24.93, 24.89, 24.68, 20.19, 13.02; $[α]_D^{22}$=+68 (c=0.21, CHCl$_3$); HRMS (FAB) m/z calcd for C$_{23}$H$_{32}$FN$_2$O$_5$ (M+H)$^+$ 435.2295. Found 435.2293.

Synthesis of LW-ART-EtC(O)—NH-5-pyrid-2-F

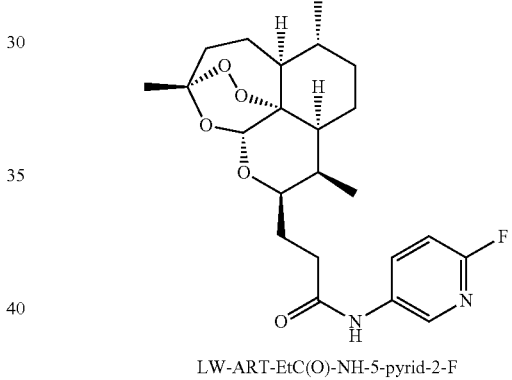

LW-ART-EtC(O)-NH-5-pyrid-2-F

A flame dried 5 mL round bottom flask was charged with carboxylic acid monomer (30 mg, 0.088 mmol), 1-(3-dimethylaminopropyl)-3-ethylcarbodiimide hydrochloride, EDC, (27 mg, 0.14 mmol), and hydroxybenzotriazole, HOBt, (15 mg, 0.11 mmol). Dichloromethane (2.5 mL) was then added and the mixture was stirred for an hour at which time, 5-amino-2-fluoropyridine (20 mg, 0.18 mmol) was added. The reaction was allowed to stir at room temperature for 3 hours. It was then quenched with 1N HCl, extracted with dichloromethane (3×5 mL), washed with brine, dried over magnesium sulfate and evaporated. The crude product was purified by preparative thin layer chromatography (silica gel, 40% EtOAc/Hexanes) to afford LW-ART-EtC(O)—NH-5-pyrid-2-F (immediately hereinabove) as an amorphous, white solid (25 mg, 0.058 mmol, 66%): IR (thin film) 3287, 2939, 2877, 1684, 1609, 1540, 1487, 1457, 1380, 1244, 1188, 1123, 1090, 1054, 1012, 938, 876 cm$^{-1}$; $^1$H NMR (400 MHz, CDCl$_3$) δ 8.41 (br. s, 1H), 8.27 (m, 2H), 6.89 (m, 1H), 5.35 (s, 1H), 4.18 (m, 1H), 2.72 (m, 1H), 2.57 (m, 2H), 2.32 (m, 1H), 2.07-1.80 (m, 5H), 1.67-1.58 (m, 2H), 1.47-1.22 (m, 7H, including singlet at 1.35), 0.95 (m, 4H), 0.89 (d, 3H, J=7.6 Hz); $^{13}$C NMR (100 MHz, CDCl$_3$) δ 171.96, 138.66, 133.34, 133.26, 109.37, 108.98, 103.57, 88.98, 81.21, 76.50, 52.31, 44.30, 37.43, 36.44, 35.89, 34.36, 30.28, 26.02, 24.88, 24.61, 20.16, 13.07; $[\alpha]_D^{25}$=+42 (c=0.17, CHCl$_3$); HRMS (FAB) m/z calcd for C$_{23}$H$_{32}$FN$_2$O$_5$ (M+H)$^+$ 435.2295. Found 435.2290.

Example 2

Synthesis of 5-Carbon-linked, C-10 Non-acetal Trioxane Dimer Esters

Preparation of 5-Carbon-Linked Trioxane Dimer Alcohol (11)

Referring now to Scheme 4, a 10-mL round-bottomed flask was charged with dihydroartemisinin acetate 2d (270.0 mg, 0.87 mmol) and linker 10 (150.0 mg, 0.52 eq) in 3 mL of CH$_2$Cl$_2$ and then cooled to −78° C. To the mixture was added a tin(IV) chloride solution (1M in CH$_2$Cl$_2$ 1.74 mL, 2 eq) dropwise over 10 min. After stirring for 50 min, the reaction mixture was quenched with NaHCO$_3$ (aq), extracted with CH$_2$Cl$_2$, dried over MgSO$_4$, and then concentrated. The crude product (ββ: αα=11:1) was purified by silica gel chromatography (ethyl acetate/hexane 1/3) to give 165.0 mg (59% yield) of dimer alcohol 11 as a white solid. $^1$H NMR: (400 MHz, CDCl$_3$): 5.32 (dd, J=512 Hz, 4 Hz, 2H), 5.29 (s, 2H), 5.16 (d, J=512 Hz, 2H), 4.71 (s, 1H), 4.50-4.47 (m, 1H), 4.41-4.36 (m, 1H), 2.68-2.65 (m, 2H), 2.34-2.25 (m, 3H), 2.21-2.12 (m, 2H), 2.07-1.99 (m, 3H), 1.91-1.88 (m, 2H), 1.79-1.75 (m, 2H), 1.66-1.59 (m, 4H), 1.46-1.35 (m, 8H including singlet 6H), 1.30-1.21 (m, 6H), 0.98-0.91 (m, 2H), 0.95 (d, J=54 Hz, 6H), 0.87 (d, J=58 Hz, 6H); $^{13}$C NMR: (100 MHz, CDCl$_3$): 147.80, 147.61, 114.84, 112.32, 103.14, 103.01, 89.22, 89.12, 81.05, 81.01, 77.95, 75.53, 74.08, 52.21, 52.18, 44.24, 44.15, 37.48, 37.45, 36.61, 36.51, 34.45, 34.40, 32.39, 31.40, 30.52, 30.50, 29.67, 25.94, 25.89, 24.83, 24.76, 24.74, 24.69, 20.14, 13.05, 12.83; HRMS (FAB) calcd for C$_{37}$H$_{56}$O$_9$ [(M+H)$^+$] 645.40026. Found, 645.39919; $[\alpha]_D^{25.1}$+105.11 (c=0.9, CHCl$_3$); IR (thin film) 3457, 2937, 2874, 1450, 1378, 1206, 1124, 1090, 1052, 1007, 942, 877; mp: 51-59° C.

Preparation of Nitrobenzoate Ester (12a)

A 10-mL round-bottomed flask was sequentially charged with dimer alcohol 11 (46.0 mg, 0.071 mmol), p-nitrobenzoyl chloride (67.0 mg, 5 eq) and a catalytic amount of 4-dimethylaminopyridine (DMAP) in 1 mL of CH$_2$Cl$_2$ at room temperature. Finally, triethylamine (0.1 mL, 10 eq) was added to the reaction mixture. The reaction mixture was stirred for 4 h and then quenched with NH$_4$Cl (aq), extracted with EtOAc, dried over MgSO$_4$, and then concentrated. The crude product was purified by column chromatography (ethyl acetate/hexane 1/8) to give 48.0 mg (85% yield) of ester 12a as a white solid. Trituration with Et$_2$O gave crystalline ester 12a for x-ray crystallography. $^1$H NMR: (400 MHz, CDCl$_3$): 8.29-8.22 (m, 5H), 6.02 (s, 1H), 5.38 (s, 2H), 5.35 (s, 1H), 5.34 (s, 1H), 5.30-5.28 (m, 2H), 4.65-4.53 (m, 2H), 2.67-2.57 (m, 2H), 2.39-2.25 (m, 4H), 2.19-2.15 (m, 2H), 2.01-1.97 (m, 2H), 1.91-1.88 (m, 2H), 1.78-1.75 (m, 2H), 1.65-1.62 (m, 4H), 1.42-1.35 (m, 8H including two singlets 6H), 1.28-1.21 (m, 6H), 0.98-0.91 (m, 2H), 0.94 (d, J=58 Hz, 6H), 0.87 (d, J=54 Hz, 3H), 0.85 (d, J=58 Hz, 3H); $^{13}$C NMR: (100 MHz, CDCl$_3$): 163.1, 150.4, 142.45, 142.25, 135.9, 130.7, 123.5, 115.5, 114.5, 102.84, 102.81, 89.54, 89.36, 81.01, 80.88, 72.48, 71.59, 52.06, 51.99, 44.03, 43.97, 37.44 37.42, 36.64, 36.58, 34.35, 32.34, 31.11, 30.44, 30.42, 25.88, 25.84, 24.81, 24.73, 20.07, 20.04, 12.70, 12.60. $[\alpha]_D^{23.4}$+43.50° (c=1.6, CHCl$_3$); IR (thin film) 2939, 1728, 1528, 1454, 1376, 1346, 1269, 1101, 1008, 877; HRMS (ESI) m/z calcd for C$_{44}$H$_{59}$NO$_{12}$Na (M+Na)+816.3929. Found 816.3914; mp: 137-144° C.

Preparation of Dinitrobenzoate Ester (12b)

A 10-mL round-bottomed flask was charged with dimer alcohol 11 (20.0 mg, 0.031 mmol), 3,4-dinitrobenzoic acid (13.0 mg, 2 eq), N-(3-dimethylaminopropyl)-N'-ethylcarbodiimide hydrochloride (EDC, 12.0 mg, 2 eq) and a catalytic amount of 4-dimethylaminopyridine (DMAP) in 1 mL of CH$_2$Cl$_2$ at room temperature. The reaction mixture was stirred for 2 h and then quenched with H$_2$O, extracted with EtOAc, dried over MgSO$_4$, and concentrated. The crude product was purified by column chromatography (ethyl acetate/hexane 1/8) to give 17.0 mg (65% yield) of dinitrobenzoate ester 12b as an amorphous solid. $^1$H NMR: (400 MHz, CDCl$_3$): 8.62 (d, J=54 Hz, 1H), 8.45 (d, J=58 Hz, 1H), 7.97 (d, J=58 Hz, 1H), 6.08 (s, 1H), 5.39-5.36 (m, 4H), 5.30 (s, 1H), 5.24 (s, 1H), 4.67-4.54 (m, 2H), 2.66-2.51 (m, 2H), 2.35-2.25 (m, 4H), 2.19-2.15 (m, 2H), 2.02-1.96 (m, 2H), 1.93-1.87 (m, 2H), 1.81-1.73 (m, 2H), 1.68-1.61 (m, 4H), 1.36 (s, 3H), 1.34 (s, 3H), 1.29-1.19 (m, 10H), 0.97-0.92 (m, 2H), 0.96 (d, J=54 Hz, 6H), 0.89 (d, J=54 Hz, 3H), 0.87 (d, J=54 Hz, 3H); $^{13}$C NMR: (100 MHz, CDCl$_3$): 161.27, 142.28, 142.04, 135.61, 134.55, 126.41, 125.17, 116.1, 115.4, 102.84, 102.77, 89.67, 89.53, 81.78, 81.10, 81.05, 72.58, 71.72, 52.03, 51.92, 43.94, 43.84, 37.51 37.49, 36.59, 34.36, 32.48, 30.55, 30.50, 25.84, 24.88, 24.75, 20.09, 20.04, 12.63, 12.50; $[\alpha]_D^{23.6}$+35.72° (c=1.3, CHCl$_3$); IR (thin film) 2927, 1732, 1549, 1454, 1374, 1280, 1110, 1053, 1007, 845; HRMS (ESI) m/z calcd for C$_{44}$H$_{58}$N$_2$O$_{14}$Na (M+Na)+ 861.3780. Found 861.3761.

Preparation of Sulfonylbenzoate Ester (12c)

A 10-mL round-bottomed flask was charged with dimer alcohol 11 (20.0 mg, 0.031 mmol), 4-(methylsulfonyl)benzoic acid (12.4 mg, 2 eq), EDC (12 mg, 2 eq) and a catalytic amount of 4-dimethylaminopyridine (DMAP) in 1 mL of CH$_2$Cl$_2$ at room temperature. The reaction mixture was stirred for 2 h and then quenched with H$_2$O, extracted with EtOAc, dried over MgSO$_4$, and concentrated. The crude product was purified by column chromatography (ethyl acetate/hexane 1/2) to give 19.7 mg (78% yield) of sulfonylbenzoate 12c as an amorphous solid. $^1$H NMR: (400 MHz, CDCl$_3$): 8.26 (d, J=58 Hz, 2H), 8.02 (d, J=58 Hz, 2H), 6.02 (s, 1H), 5.38 (s, 2H), 5.35 (d, J=54 Hz, 2H), 5.31 (d, J=54 Hz, 2H), 4.62-4.60 (m, 1H), 4.58-4.56 (m, 1H), 3.07 (s, 3H), 2.68-2.58 (m, 2H), 2.37-2.26 (m, 4H), 2.19-2.15 (m, 2H), 2.02-1.98 (m, 2H), 1.93-1.88 (m, 2H), 1.79-1.75 (m, 2H), 1.66-1.62 (m, 4H), 1.39-1.37 (m, 2H), 1.39 (s, 3H), 1.36 (s, 3H), 1.30-1.22 (m, 6H), 0.96-0.90 (m, 2H), 0.95 (d, J=54 Hz, 6H), 0.87 (d, J=58 Hz, 3H), 0.86 (d, J=54 Hz, 3H); $^{13}$C NMR: (100 MHz: CDCl$_3$) 163.42, 144.10, 142.52, 142.32, 135.37, 130.62, 127.48, 115.56, 114.42, 102.91, 102.86, 89.58, 89.39, 81.07, 80.83, 72.60, 71.65, 52.12, 52.05, 44.35, 44.02, 37.49 37.47, 36.68, 36.63, 34.39, 32.37, 31.08, 30.47, 25.92, 25.89, 24.85, 24.77, 20.12, 20.09, 12.77, 12.65; $[\alpha]_D^{24.5}$+ 45.01° (c=0.95, CHCl$_3$); IR (thin film) 2939, 2875, 1728, 1646, 1455, 1321, 1269, 1176, 1155, 753; HRMS (ESI) m/z calcd for C$_{45}$H$_{62}$O$_{12}$S Na(M+Na)+849.3854. Found 849.3831.

Example 3

Synthesis of Silylamide Trioxanes

Experimental

High-pressure liquid chromatography (HPLC) was performed on a Rainin HPLX system equipped with two 25-mL pump heads and a Rainin Dynamax UV-C dualbeam variable wavelength detector set at 254 using a Phenomenex Luna 5μ C18 250×10 mm column. The purity of analogs 14a, 14b, and 16 was ≥98% based on HPLC analysis. Nuclear magnetic resonance spectra were recorded on a Broker 400 MHz spectrometer with chloroform as the reference. Infrared spectra were obtained using a Perkin-Elmer Series FT-IR instrument. Optical rotation measurements were taken on a Jasco P-1010 polarimeter. Mass spectroscopy data were obtained using a VG-70S magnetic sector mass spectrometer.

Synthesis of monomer LW-ART-EtC(O)—NHCH$_2$SiMe$_3$ (14a).

Monomer acid ART-EtC(O)—OH (13, Woodard et al., 2009, 0.60 g, 1.8 mmol), 1-(3-dimethylaminopropyl)-3-ethylcarbodiimide hydrochloride (EDC, 0.55 g, 2.9 mmol), and hydroxybenzotriazole (HOBt, 0.30 g, 2.2 mmol) were charged into a flame-dried 100 mL round bottom flask at room temperature. Dichloromethane (37 mL) was then added and the mixture was stirred for an hour at which time, (trimethylsilyl)methylamine (0.48 mL, 3.6 mmol) was added by syringe. The reaction was allowed to stir at room temperature for 3 hours. It was then quenched with 1N HCl, extracted with dichloromethane (3×5 mL), washed with brine, dried over magnesium sulfate and evaporated. The crude product was purified by preparative thin layer chromatography (silica gel, 40% EtOAc/Hexanes) to afford LW-ART-EtC(O)—NHCH$_2$SiMe$_3$ (14a) as an amorphous, white solid (0.72 g, 1.7 mmol, 94%): IR (thin film) 3295, 2951, 2876, 1743, 1637, 1547, 1451, 1376, 1279, 1249, 1189, 1126, 1094, 1057, 1011, 946, 911, 853 cm$^{-1}$; 1H-NMR (400 MHz, CDCl$_3$) δ 5.67 (br. s, 1H), 5.26 (s, 1H), 4.04 (m, 1H), 2.74-2.66 (m, 3H), 2.44 (m, 1H), 2.33-2.21 (m, 2H), 2.01-1.74 (m, 5H), 1.63-1.51 (m, 2H), 1.46-1.17 (m, 7H, including singlet at 1.36), 0.95-0.91 (m, 4H), 0.84 (d, 3H, J=7.6 Hz), 0.03 (s, 9H); $^{13}$C-NMR (100 MHz, CDCl$_3$) δ 173.20, 103.36, 88.74, 81.13, 75.98, 52.42, 44.45, 37.38, 36.50, 34.55, 34.43, 30.14, 29.78, 26.17, 25.26, 24.85, 24.63, 20.20, 13.15, -2.63; [α]$_D^{23}$=+61 (c=0.23, CHCl$_3$); HRMS (FAB) m/z calcd for C22H39NO5Si (M)+ 425.2598. Found 425.2584.

Synthesis of monomer LW-ART-EtC(O)—NH(CH$_2$)$_3$SiMe$_3$ (14b).

Monomer acid ART-EtC(O)—OH (13, Woodard et al., 2009, 30 mg, 0.088 mmol), EDC (27 mg, 0.14 mmol), and HOBt (15 mg, 0.11 mmol) were charged into a flame-dried 5 mL round bottom flask at room temperature. Dichloromethane (2.5 mL) was then added and the mixture was stirred for an hour at which time, 3-aminopropyltrimethylsilane (24 mg, 0.18 mmol) was added by syringe. The reaction was allowed to stir at room temperature for 3 hours. It was then quenched with 1N HCl, extracted with dichloromethane (3×5 mL), washed with brine, dried over magnesium sulfate and evaporated. The crude product was purified by preparative thin layer chromatography (silica gel, 40% EtOAc/hexanes) to afford LW-ART-EtC(O)—NH(CH$_2$)$_3$SiMe$_3$ (14b) as an amorphous, white solid (42 mg, 0.088 mmol, 100%): IR (thin film) 3304, 2951, 2875, 1644, 1547, 1452, 1376, 1248, 1222, 1188, 1126, 1096, 1057, 1012, 938, 912, 862, 837, 753 cm-1; 1H-NMR (400 MHz, CDCl$_3$) δ 5.82 (br. s, 1H), 5.27 (s, 1H), 4.03 (m, 1H), 3.18 (m, 2H), 2.70 (m, 1H), 2.46-2.39 (m, 1H), 2.34-2.21 (m, 2H), 2.01-1.76 (m, 5H), 1.64-1.18 (m, 11H, including singlet at 1.37), 0.95-0.92 (m, 4H), 0.85 (d, 3H, J=7.6 Hz), 0.45 (m, 2H), -0.04 (s, 9H); $^{13}$C-NMR (100 MHz, CDCl$_3$) δ 172.91, 103.37, 88.71, 81.16, 76.10, 52.43, 44.47, 42.72, 37.39, 36.52, 34.72, 34.44, 30.17, 26.17, 25.02, 24.86, 24.64, 24.17, 20.21, 13.84, 13.19, -1.76; [α]$_D^{23}$=+64 (c=0.24, CHCl$_3$); HRMS (FAB) m/z calcd for C$_{24}$H$_{44}$NO$_5$Si (M+H)+ 454.2989. Found 454.2980.

Synthesis of dimer BTM-isobu-C(O)NHCH$_2$SiMe$_3$ (16).

Carboxylic acid dimer 15 (15 mg, 0.03 mmol), EDC (4.4 mg, 0.03 mmol, 1.1 eq) and HOBt (3.8 mg, 0.03 mmol, 1.1 eq) were charged into a flame dried 5 mL round bottom flask at room temperature. Dichloromethane (1 mL) and (trimethylsilyl)methylamine (4 mL, 0.03 mmol, 1.1 eq) were added, and the reaction mixture was stirred at rt for 2 hours. The reaction mixture was further diluted with CH$_2$Cl$_2$, and the organic layer was washed with water and sat. aq. NaCl, extracted, dried on MgSO$_4$, filtered, and the solvent was removed under reduced pressure. The residue was purified directly on silica. Isocratic elution (25% ethyl acetate in hexanes) afforded the desired product as an amorphous, colorless solid: (17.8 mg, 0.03 mmol, 100%): IR (thin film) 3315, 2950, 2875, 1716, 1647, 1540, 1456, 1375, 1249, 1205, 1124, 1093, 1052, 1011, 939, 856; $^1$H-NMR (400 MHz, CDCl$_3$) d 5.97 (t, 1H, J=5.08 Hz), 5.26 (s, 1H), 5.24 (s, 1H), 4.09 (m, 1H), 3.98 (m, 1H), 2.82 (dd, 1H, J=5.94, 15.28), 2.72 (sextet, 2H, J=6.67), 2.66 (dd, 1H, J=5.05, 15.16), 2.58 (m, 1H), 2.32 (td, 2H, J=3.71, 13.96), 2.05 (m, 4H), 1.86 (m, 4H), 1.74 (m, 4H), 1.63 (m, 6H), 1.51 (m, 6H), 1.39 (m, 9H, including singlets at 1.40 and 1.37), 1.25 (m, 6H), 0.94 (m, 6H), 0.84 (m, 4H), 0.07 (s, 9H); $^{13}$C-NMR (100 MHz, CDCl$_3$) 0175.87, 103.46, 103.44, 101.08, 88.38, 88.29, 81.19, 81.01, 75.87, 74.26, 52.56, 52.54, 44.76, 44.69, 37.33, 37.26, 36.62, 36.51, 34.51, 29.79, 29.77, 29.71, 26.19, 26.11, 24.73, 24.66, 24.59, 24.56, 20.22, 13.24, -2.42; [α]$_D^{23}$=+59 (c=0.69, CHCl$_3$); HRMS (FAB) m/z calcd for C$_{38}$H$_{63}$NO$_9$Si (M+H) 706.4348. Found 706.4350.

Example 4

Synthesis of Trioxane Dimer Orthoesters

Example 4A

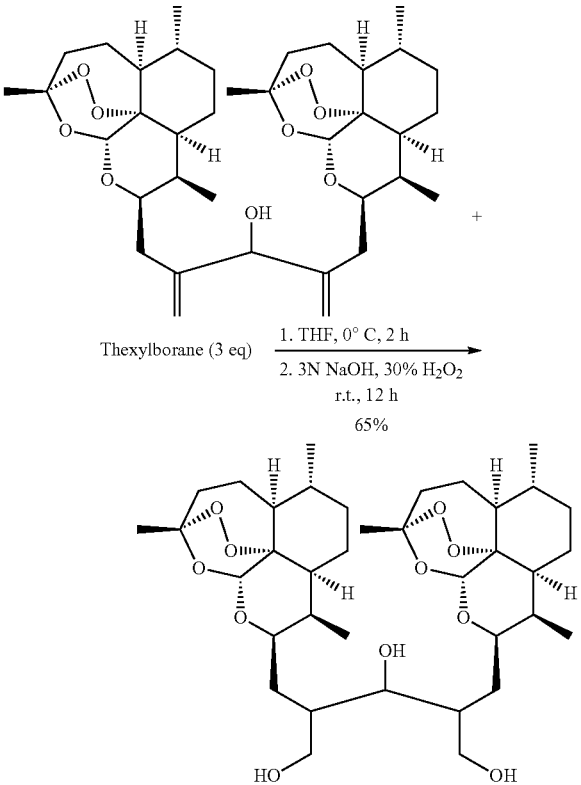

A 10 mL round-bottomed flask was charged with 5-carbon linked dimer alcohol (57 mg, 0.0885 mmol) in 1 mL of THF. To the reaction mixture was added thexylborane (0.8 mL, 3 eq.) 0.33M in THF solution obtained from BH₃THF (1 eq) and 2,3-dimethyl-2-butene (2 eq) at 0° C. for 1 hr. The reaction mixture was stirred for 2 hr and then added 3 N NaOH (0.15 mL, 5 eq) and 30% H₂O₂ (0.15 mL, 5 eq). The reaction mixture was warmed to room temperature and then stirred for 12 hr. The reaction mixture was quenched with H₂O, extracted with EtOAc, dried over MgSO₄ and concentrated. The crude product was purified by column chromatography (EtOAc/Hexane=3/1) to give 39.2 mg in 65% yield.

¹H NMR: (400 MHz, CDCl₃): 5.33 (d, J=12, 2H), 4.49-4.47 (m, 1H), 4.42-4.38 (m, 1H), 4.00-3.94 (m, 3H), 3.78-3.74 (m, 1H), 2.93 (bs, 3H), 2.63-2.57 (m, 2H), 2.35-2.28 (m, 2H), 2.12-2.08 (m, 1H), 2.03-1.98 (m, 2H), 1.96-1.88 (m, 3H), 1.83-1.55 (m, 10H), 1.45-1.35 (m, 4H), 1.40 (s, 6H), 1.27-1.24 (m, 4H), 0.96 (s, 3H), 0.95 (s, 3H), 0.93-91 (m, 2H), 0.90 (d, J=4 Hz, 3H), 0.86 (d, J=8 Hz, 3H).

Example 4B

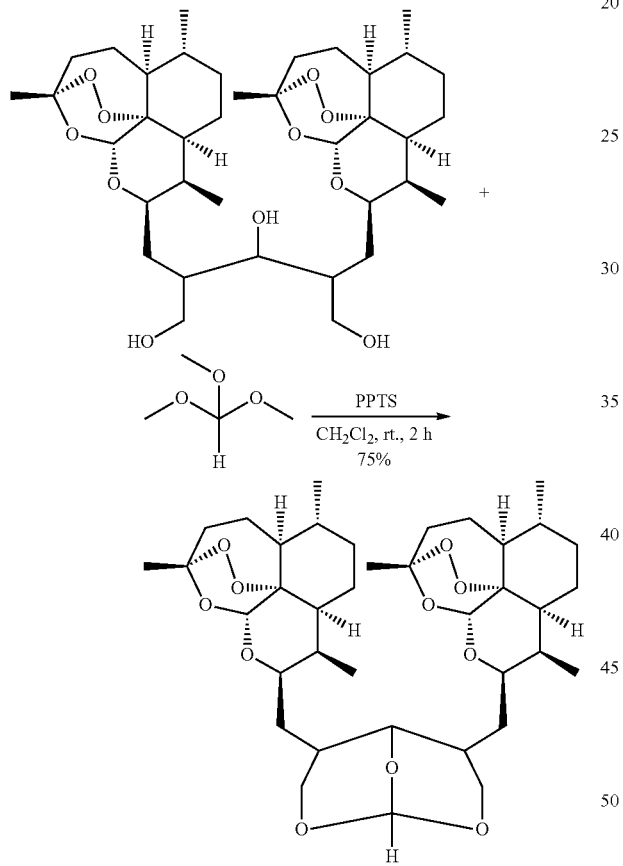

A 10 mL round-bottomed flask was charged with 5-carbon linked dimer triol (9.3 mg, 0.0137 mmol) and trimethylorthoformate (4.5 µL, 3 eq, Aldrich anhydrous 99.8%) in 1 mL of CH₂Cl₂. To the reaction mixture was added pyridinium p-toluenesulfonate (PPTS, catalytic amount) at room temperature. The reaction mixture was stirred for 2 h and then quenched with NaHCO₃(aq), extracted with EtOAc, dried over MgSO₄ and concentrated. The crude product was purified by column chromatography (EtOAc/Hexane=1/3) to give 7.1 mg in 75% yield.

¹H NMR: (400 MHz, Benzene-d6): 6.16 (s, 1H), 5.35 (s, 1H), 5.30 (s, 1H), 4.53-4.47 (m, 3H), 4.40-4.36 (m, 1H), 4.08 (s, 1H), 3.85-3.81 (m, 1H), 3.64-3.60 (m, 1H), 2.83-2.78 (m, 1H), 2.53-2.48 (m, 1H), 2.32-2.18 (m, 3H), 2.08-2.03 (m, 1H), 1.96-1.85 (m, 2H), 1.77-1.68 (m, 3H), 1.62-1.44 (m, 10H), 1.42 (s, 3H), 1.40 (s, 3H), 1.29-1.23 (m, 3H), 1.12-1.03 (m, 5H), 0.74 (d, J=4 Hz, 3H), 0.71 (d, J=8 Hz, 3H), 0.68 (d, J=8 Hz, 3H), 0.65 (d, J=8 Hz, 3H), 0.62-0.57 (m, 2H).

HRMS (FAB) m/z calcd for C₃₈H₅₈O₁₁ (M+H)+ 691.4057. Found 691.4051.

Example 4C

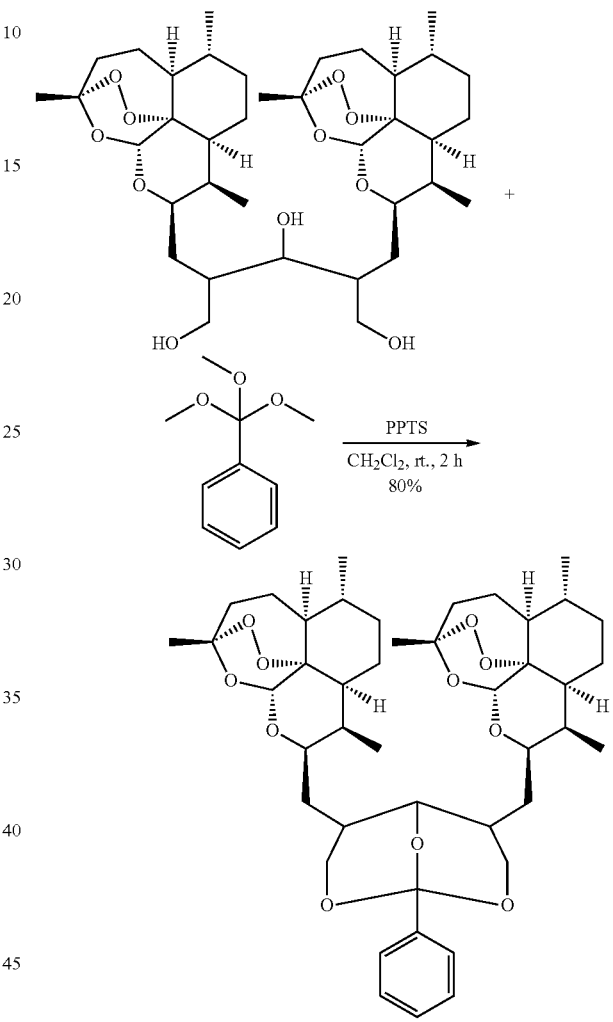

A 10 mL round-bottomed flask was charged with 5-carbon linked dimer triol (8.2 mg, 0.012 mmol) and trimethylorthobenzoate (6.5 µL, 3 eq, Aldrich 98%) in 1 mL of CH₂Cl₂. To the reaction mixture was added pyridinium p-toluenesulfonate (PPTS, catalytic amount) at room temperature. The reaction mixture was stirred for 2 hr and then quenched with NaHCO₃ (aq), extracted with ETOAc, dried over MgSO₄ and concentrated. The crude product was purified by column chromatography (EtOAc/Hexane=1/5) to give 7.4 mg in 80% yield.

¹H NMR: (400 MHz, Acetone-d6): 7.58-7.55 (m, 2H), 7.33-7.31 (m, 3H), 5.37 (s, 2H), 4.47-4.38 (m, 3H), 4.32-4.27 (m, 1H), 4.03-4.02 (m, 1H), 3.67 (dd, J=12 Hz, 8 Hz, 2H), 2.65-2.58 (m, 1H), 2.54-2.47 (m, 1H), 2.29-2.18 (m, 2H), 2.15-2.11 (m, 1H), 2.08-2.02 (m, 3H), 2.00-1.97 (m, 1H), 1.93-1.84 (m, 4H), 1.82-1.73 (m, 4H), 1.69-1.59 (m, 4H), 1.57-1.53 (m, 1H), 1.44-1.37 (m, 4H), 1.34 (s, 3H), 1.31 (s, 3H), 1.25-1.17 (m, 2H), 0.98-0.95 (m, 2H), 0.96 (d, J=4 Hz, 3H), 0.93 (d, J=4 Hz, 3H), 0.91 (d, J=4 Hz, 3H), 0.89 (d, J=4 Hz, 3H).

$^{13}$C NMR: (400 MHz, Acetone-d6): 142.12, 129.23, 128.43, 126.14, 110.61, 103.42, 103.16, 90.48, 89.77, 81.67, 81.59, 77.86, 73.99, 72.55, 63.13, 61.51, 54.92, 53.30, 52.95, 45.33, 44.86, 39.45, 39.03, 37.98, 37.86, 37.35, 35.28, 35.18, 32.21, 31.95, 31.60, 31.40, 26.32, 25.60, 25.51, 25.44, 25.38, 20.43, 20.32, 13.32, 12.86.

Example 4D

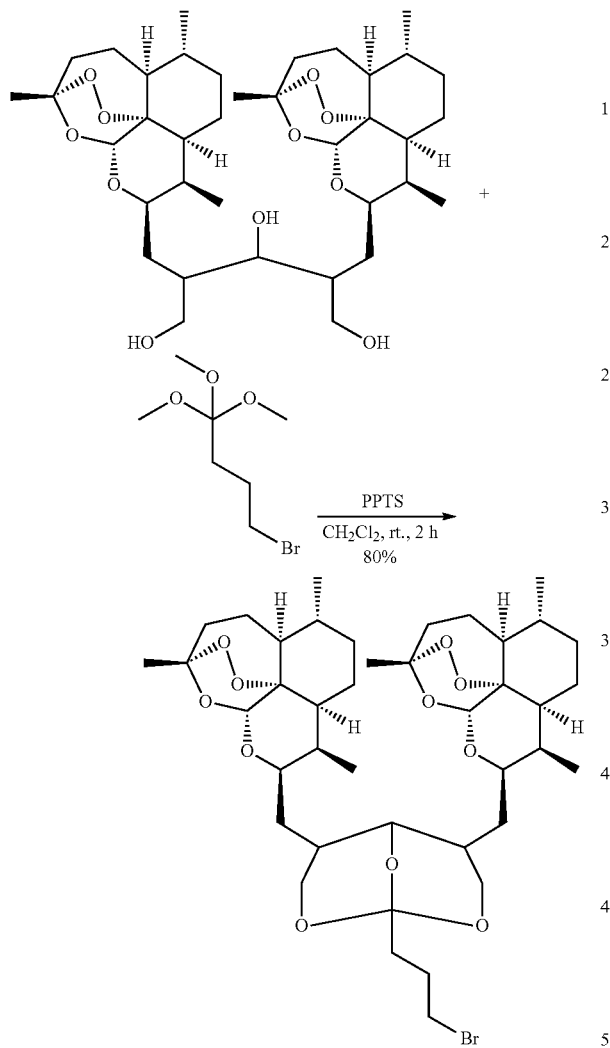

A 10 mL round-bottomed flask was charged with 5-carbon linked dimer triol (10.5 mg, 0.0154 mmol) and trimethyl 4-bromoorthobutyrate (8 μL, 3 eq, Aldrich 95%) in 1 mL of CH$_2$Cl$_2$. To the reaction mixture was added pyridinium p-toluenesulfonate (PPTS, catalytic amount) at room temperature. The reaction mixture was stirred for 2 h and then quenched with NaHCO$_3$(aq), extracted with EtOAc, dried over MgSO$_4$ and concentrated. The crude product was purified by column chromatography (EtOAc/Hexane=1/3) to give 10 mg in 80% yield.

$^1$H NMR: (400 MHz, Acetone-d6): 5.37 (d, J=4 Hz, 2H), 4.41-4.36 (m, 1H), 4.30-4.22 (m, 3H), 3.90-3.88 (m, 1H), 3.58-3.51 (m, 4H), 2.65-2.60 (m, 1H), 2.53-2.48 (m, 1H), 2.30-2.22 (m, 2H), 2.08-2.06 (m, 3H), 2.04-2.01 (m, 3H), 1.96-1.88 (m, 3H), 1.84-1.77 (m, 4H), 1.76-1.72 (m, 2H), 1.69-1.63 (m, 5H), 1.62-1.55 (m, 1H), 1.47-1.38 (m, 5H), 1.36 (s, 3H), 1.33 (s, 3H), 1.25-1.17 (m, 2H), 0.99-0.97 (m, 2H), 0.98 (d, J=4 Hz, 3H), 0.96 (d, J=4 Hz, 3H), 0.92 (d, J=4 Hz, 3H), 0.90 (d, J=4 Hz, 3H).

$^{13}$C NMR: (400 MHz, Acetone-d6): 111.85, 103.40, 103.14, 90.40, 89.69, 81.63, 81.55, 77.05, 74.05, 72.65, 62.52, 61.11, 54.92, 53.28, 52.93, 45.85, 44.85, 39.33, 39.01, 38.29, 37.96, 37.86, 37.33, 35.26, 35.16, 34.87, 32.09, 31.75, 31.56, 31.37, 27.74, 26.31, 25.58, 25.49, 25.42, 25.37, 20.44, 20.33, 13.32, 12.86.

Example 4E

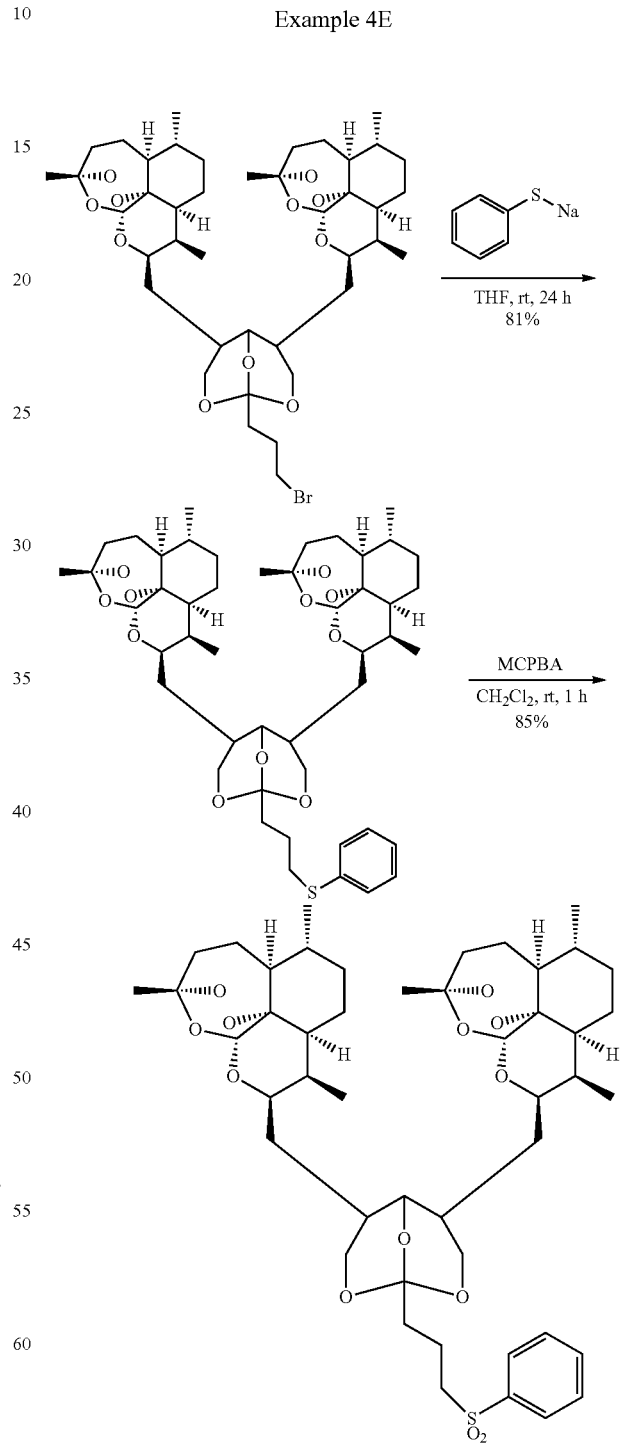

A 10 mL round-bottomed flask was charged with bromo orther-dimer (4 mg, 0.005 mmol) and sodium benzenethiolate[1.3 mg, 2 eq, Preparation: NaH (1.1 eq) and thiophenol in THF 0° C. for 30 min. Filtration with diethyl ether and then drying] in 1 mL of THF at room temperature. The reaction mixture was stirred for 24 h and then quenched with $H_2O$, extracted with EtOAc, dried over $MgSO_4$ and concentrated. The crude product was purified by column chromatography (EtOAc/Hexane=1/5) to give 3.4 mg in 81% yield. A 10 mL round-bottomed flask was charged with thiophenyl ortho-dimer (3.4 mg, 0.004 mmol) and 3-chloroperbenzoic acid (MCPBA, 3.0 mg, 3 eq) in 1 mL of $CH_2Cl_2$ at room temperature. The reaction mixture was stirred for 1 h and then quenched with $NaHCO_3$ (aq), extracted with EtOAc, dried over $MgSO_4$ and concentrated. The crude product was purified by column chromatography (EtOAc/Hexane=1/2) to give 3.0 mg in 85% yield.

$^1$H NMR: (400 MHz, Acetone-d6): 7.95-7.93 (m, 2H), 7.77-7.75 (m, 1H), 7.71-7.67 (m, 2H), 5.37 (d, J=4 Hz, 2H), 4.39-4.33 (m, 1H), 4.26-4.17 (m, 3H), 3.86-3.85 (m, 1H), 3.51-3.44 (m, 2H), 3.29-3.25 (m, 2H), 2.65-2.58 (m, 1H), 2.53-2.47 (m, 1H), 2.29-2.21 (m, 2H), 2.08-2.06 (m, 3H), 2.04-2.01 (m, 3H), 1.96-1.88 (m, 3H), 1.84-1.77 (m, 4H), 1.76-1.72 (m, 2H), 1.69-1.63 (m, 5H), 1.62-1.55 (m, 1H), 1.46-1.38 (m, 5H), 1.35 (s, 3H), 1.32 (s, 3H), 1.25-1.18 (m, 2H), 0.99-0.97 (m, 2H), 0.98 (d, J=4 Hz, 3H), 0.96 (d, J=4 Hz, 3H), 0.91 (d, J=4 Hz, 3H), 0.89 (d, J=4 Hz, 3H).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Adjuik, M.; Babiker, A.; Garner, P.; Olliaro, P.; Taylor, W.; White, N., Artesunate combinations for treatment of malaria: meta-analysis *Lancet* 2004, 363, 9-17.

Arinaitwe, E.; Sandison, T. G.; Wanzira, H.; Kakuru, A.; Homsy, J.; Kalamya, J.; Kamya, M. R.; Vora, N.; Greenhouse, B.; Rosenthal, P. J.; Tappero, J.; Dorsey, G. Artemether-Lumefantrine versus Dihydroartemisinin-Piperaquine for Falciparum Malaria: A Longitudinal, Randomized Trial in Young Ugandan Children. *Clin. Infect. Dis.* 2009, 49, 1629-1637.

Ashley, E. A.; White, N. J. Artemisinin-based combinations *Curr. Opin. Infect. Dis.* 2005, 18, 531-536.

Bachmann, S., J. Schroder, C. Bottmer, E. F., Torrey, and R. H. Yolken. 2005. Psychopathology in first-episode schizophrenia and antibodies to *Toxoplasma gondii*. Psychopathol. 38(2):87-90.

Bégué J-P, Bonnet-Delpon D. Fluoroartemisinins: metabolically more stable antimalarial artemisinin derivatives. *Chem Med Chem* 2007, 2, 608-624.

Berens, R. L., E. C. Krug, P. B. Nash, and T. J. Curiel. 1998. Selection and characterization of *Toxoplasma gondii* mutants resistant to artemisinin. J. Infect. Dis. 177:1128-1131.

Bigot A, Breit B. A convenient allylic functionalization of bis(prop-2-enyl)methanol by direct trimetalation. *Synthesis* 2008, 22, 3692-3696.

Chadwick J, Mercer A E, Park B K, Cosstick R, O'Neill P M. 2009. Synthesis and biological evaluation of extraordinarily potent C-10 carba artemisinin dimers against P-falciparum malaria parasites and HL-60 cancer cells. *Bioorg Med Chem* 17: 1325-1338.

Chang, H. R., C. W. Jefford, and J.-C. Pechere. 1989. In vitro effects of three new 1,2,4-trioxanes (pentatroxane, thiahexatroxane, and hexatroxanone) on *Toxoplasma gondii*. Antimicrob. Agents Chemother. 33(10): 1748-1752.

Chen, X.; Chong, C. R.; Shi, 1.; Yoshimoto, T.; Sullivan, D. J., Jr.; Lin, J. O. Inhibitors of *Plasmodium falciparum* methionine aminopeptidase 1b possess antimalarial activity *Proc. Natl. Acad. Sci. U.S.A.* 2006, 103, 14548-14553.

de Pilla Varotti, F.; Botelho, A. C. C.; Andrade, A. A.; de Paula, R. C.; Fagundes, E. M. S.; Valverde, A.; Mayer, L. M. U.; Mendonca, J. S.; de Souza, M. V. N.; Boechat, N.; Krettli, A. U. Synthesis, antimalarial activity, and intracellular targets of MEFAS, a new hybrid compound derived from mefloquine and artesunate *Antimicrob. Agents Chemother.* 2008, 52, 3868-3874.

Eastman, R. T.; Fidock, D. A. Artemisinin-based Combination Therapies: A Vital Tool in Efforts to Eliminate Malaria. *Nat. Rev. Micro.* 2009, 7, 864-874.

Fanello, C. I.; Karema, C.; van Doren, W.; Van Overmeir, C.; Ngamije, D.; D'Alessandro, U. A randomised trial to assess the safety and efficacy of artemether-lumefantrine (Coartem®) for the treatment of uncomplicated *Plasmodium falciparum* malaria in Rwanda. *Trans. R. Soc. Trop. Med. Hyg.* 2007, 101, 344-350.

Gautam, A.; Ahmed, T.; Batra, V.; Paliwal, J., Pharmacokinetics and Pharmacodynamics of Endoperoxide Antimalarials *Curr. Drug. Metab.* 2009, 10, 289-306

Gately, S.; West, R. Novel Therapeutics With Enhanced Biological Activity Generated by the Strategic Introduction of Silicon Isosteres into Known Drug Scaffolds. *Drug Dev. Res.* 2007, 68, 156-163.

Gelb M. H. Drug discovery for malaria: a very challenging endeavor. *Curr Opin Chem Biol* 2007, 11, 440-445.

Georgiev, V. S. 1994. Management of toxoplasmosis. Drugs. 48(2):179-188.

Guthmann, J.-P.; Cohuet, S.; Rigutto, C.; Fortes, F.; Saraiva, N.; Kiguli, J.; Kyomuhendo, J.; Francis, M.; Noel, F.; Mulemba, M. Balkan, S. High efficacy of two artemisinin-based combinations (artesunate+amodiaquine and artemether+lumefantrine) in Caala, Central Angola *Am. J. Trop. Med. Hyg.* 2006, 75, 143-145.

Haynes, R. K. From artemisinin to new artemisinin antimalarials: biosynthesis, extraction, old and new derivatives, stereochemistry and medicinal chemistry requirements. *Curr Top Med Chem* 2006, 6, 509-537.

Hof, Fraser; Schatz, Andri; Fah, Christoph; Meyer, Solange; Bur, Daniel; Liu, Jun; Goldberg, D. E.; Diederich, F. Starving the Malaria Parasite: Inhibitors Active Against the Aspartic Proteases Plasmepsins I, II, and IV. *Angew. Chem. Int. Ed.* 2006, 45, 2138-2141.

Holfels, E., J. McAuley, D. Mack, W. K. Milhous, and R. McLeod. 1994. In vitro effects of artemisinin ether, cycloguanil hydrochloride (alone and in combination with sulfadiazine), quinine sulfate, mefloquine, primaquine phosphate, trifluoperazine hydrochloride, and verapamil on *Toxoplasma gondii*. Antimicrob. Agents Chemother. 38(6):1392-1396.

Jefford, C. W. Synthetic peroxides as antimalarials. *Curr Opin Invest Drugs* (*Thomson Sci.*) 2004, 5, 866-872.

Jones-Brando, L., E. F. Torrey, and R. Yolken. 2003. Drugs used in the treatment of schizophrenia and bipolar disorder inhibit the replication of *Toxoplasma gondii*. Schizophr. Res. 62:237-244.

Jung, M.; Lee, S.; Ham, J.; Lee, K.; Kim, H.; Kim, S. K., Antitumor activity of novel deoxoartesmisinin monomers, dimers, and trimer *J. Med. Chem.* 2003, 46, 987-994.

Kelly, J. X.; Smilkstein, M. J.; Brun, R.; Wittlin, S.; Cooper, R. A.; Lane, K. D.; Janowsky, A.; Johnson, R. A.; Dodean, R. A.; Winter, R.; Hinrichs, D. J.; Riscoe, M. K. Discovery of dual function acridones as a new antimalarial chemotype. *Nature* 2009, 459, 270-273.

Klayman, D. L. Qinghaosu (artemisinin): an antimalarial drug from China. *Science* 1985, 228, 1049-1055.

LeBlanc, R.; Vasquez, Y.; Hannaman, D.; Kumar, N. Markedly Enhanced Immunogenicity of a Pfs25 DNA Based Malaria Transmission Blocking Vaccine by in Vivo Electroporation. *Vaccine* 2008, 26, 185-192.

Lin A. J., D. L. Klayman, and W. K Milhous. 1987. Antimalarial activity of new water-soluble dihydroartemisinin derivatives. J. Med. Chem. 30:2147-2150.

Moon, D. K.; Singhal, V.; Kumar, N.; Shapiro, T. A.; Posner, G. H. Antimalarial Preclinical Drug Development: A Single Oral Dose of A 5-Carbon-linked Trioxane Dimer Plus Mefloquine Cures Malaria-Infected Mice. *Drug Dev. Res.* 2009, in press.

Myint, H. Y.; Ashley, E. A.; Day, N. P. J.; Nosten, F.; White, N. J., Efficacy and safety of dihydroartemisinin-piperaquine *Trans. R. Soc. Trop. Med. Hyg.* 2007, 101, 858-866.

Olliaro, P. L.; Boland, P. B. Clinical public health implications of antimalarial drug resistance. In *Antimalarial Chemotherapy: Mechanisms of Action, Resistance, and New Directions in Drug Discovery*; Rosenthal, P. J., Ed.; Humana Press: Totowa, N.J., 2001; pp 65-83.

O'Neill P. M., Posner G. H. A medicinal chemistry perspective on artemisinin and related endoperoxides. *J Med Chem* 2004, 47, 2945-2964.

Ou-Yang, K., E. C. Krug, J. J. Marr, and R. L. Berens. 1990. Inhibition of growth of *Toxoplasma gondii* by Qinghaosu and derivatives. Antimicrob. Agents Chemother. 34(10): 1961-1965.

Paik I-H, Xie S, Shapiro T A, Labonte T, Sarjeant A A N, Baege A C, Posner G H. 2006. Second generation, orally active, antimalarial, artemisinin-derived trioxane dimers with high stability, efficacy, and anticancer activity. *J Med Chem* 2006, 49, 2731-2734.

Pandey, K. C.; Sijwall, P. S.; Singh, A.; Na, B.-K.; Rosenthal, P. J. Independent Intramolecular Mediators of Folding, Activity, and Inhibition for the *Plasmodium falciparum* Cysteine Protease Falcipain-2. *J. Biol. Chem.* 2004, 279, 3484-3491.

Posner, G. H.; Paik, I.-H.; Sur, S.; McRiner, A. J.; Borstnik, K.; Xie, S.; Shapiro, T. A., Orally active, antimalarial, anticancer, artemisinin-derived trioxane dimers with high stability and efficacy *J. Med. Chem.* 2003, 46, 1060-1065

Posner G. H., Paik I.-H., Chang W., Borstnik K., Sinishtaj S., Rosenthal A. S., Shapiro T. A. Malaria-infected mice are cured by a single dose of novel artemisinin derivatives. *J Med Chem* 2007, 50, 2516-2519.

Posner G. H., Chang W., Hess L., Woodard L., Sinishtaj S., Usera A. R., Maio W., Rosenthal A. S., Kalinda A. S., D'Angelo J. G., Petersen K. S., Stohler R., Chollet J., Santo-Tomas J., Synder C., Rottmann M., Wittlin S., Brun R., Shapiro T. A. Malaria-infected mice are cured by oral administration of new artemisinin derivatives. *J Med Chem* 2008, 51, 1035-1042.

Ramanathan-Girish, S.; Catz, P.; Creek, M. R.; Wu, B.; Thomas, D.; Krogstad, D. J., De, D.; Mirsalis, J. C.; Green, C. E. Pharmacokinetics of the Antimalarial Drug, AQ-13, in Rats and Cynomolgus Macaques. *Int. J. Toxicol.* 2004, 23, 179-189.

Ridley, R. G. Medical Need, Scientific Opportunity, and the Drive for Antimalarial Drugs. *Nature* 2002, 415, 686-693.

Rosenthal, A. S.; Chen, X.; Liu, J. O.; West, D. C.; Hergenrother, P. J.; Shapiro, T. A.; Posner, G. H., Malaria-infected mice are cured by a single oral dose of new dimeric trioxane sulfones which are also selectively and powerfully cytotoxic to cancer cells *J. Med. Chem.* 2009, 52, 1198-1203.

Sagara, I.; Diallo, A. D.; Kone, M.; Coulibaly, M.; Diawara, S. I.; Guindo, O.; Maiga, H.; Niambele, M. B.; Sissoko, M.; Dicko, A.; Djimde, A.; Doumbo, O. K. A randomized trial of artesunate-mefloquine versus artemether-lumefantrine for treatment of uncomplicated *Plasmodium falciparum* malaria in Mali *Am. J. Trop. Med. Hyg.* 2008, 79, 655-661.

Sagara, I.; Rulisa, S.; Mbacham, W.; Adam, I.; Sissoko, K.; Maiga, H.; Traore, O. B.; Dara, N.; Dicko, Y. T.; Dicko, A.; Djimde, A.; Jansen, F. H.; Doumbo, O. K., Efficacy and safety of a fixed dose artesunate-sulphamethoxypyrazine-pyrimethamine compared to artemether-lumefantrine for the treatment of uncomplicated *falciparum* malaria across Africa: a randomized multicentre trial *Malar. J.* 2009, 8, 63-73.

Shizhen L. 2003. *Compendium of Materia Medica (Bencao Gangmu); first published in Chinese in* 1593, *translation published* 2003. Beijing, China: Foreign Languages Press.

Sirima, S. B.; Tiono, A. B.; Gansane, A.; Diarra, A.; Ouedraogo, A.; Konate, A. T.; Kiechel, J. R.; Morgan, C. C.; Olliaro, P. L.; Taylor, W. R. J. *Malar. J.* 2009, 8, 48.

Souares A., Lalou R., Sene I., Sow D., Le Hesran J.-Y. 2009. Factors related to compliance to anti-malarial drug combination: example of amodiaquine/sulphadoxine-pyrimethamine among children in rural Senegal. *Malar J* 2009, 8, 118-125.

Tang Y, Dong Y, Vennerstrom J L. 2004. Synthetic peroxides as antimalarials. *Med Res Rev* 2004, 24, 425-448.

Tenter, A. M., A. R. Heckeroth, and L. M. Weiss. 2000. *Toxoplasma gondii*: from animals to humans. Intl. J. Parasitol. 30:1217-1258.

Torrey E F, Bartko J J, Lun Z R, Yolken R H. 2007. Antibodies to *Toxoplasma gondii* in patients with schizophrenia: a meta-analysis. Schizophr Bull. 33(3):729-736.

Troye-Blomberg, M.; Berzins, K. Rational Vaccine Development against Malaria. *Microbes Infect.* 2007, 9, 749-750.

Vennerstrom, J. L.; Arbe-Barnes, S.; Brun, R.; Charman, S. A.; Chiu, F. C. K.; Chollet, J.; Dong, Y.; Dorn, A.; Hunziker, D.; Matile, H.; McIntosh, K.; Padmanilayam, M.; Santo, T. J.; Scheurer, C.; Scorneaux, B.; Tang, Y.; Urwyler, H.; Wittlin, S.; Charman, W. N., Identification of an antimalarial synthetic trioxolane drug development candidate *Nature* 2004, 430, 900-904.

World Health Organization. *Guidelines for the Treatment of Malaria*; WHO: Geneva, Switzerland, 2006.

Woodard, L. E.; Chang, W.; Chem, X.; Liu, J. O.; Shapiro, T. A.; Posner, G. H. Malaria-Infected Mice Live until at Least Day 30 after a New Monomeric Trioxane Combined with Mefloquine are Administered Together in a Single Low Dose. *J. Med. Chem.* 2009, 52, in press.

Yearick, K.; Ekoue-Kovi, K.; Iwaniuk, D. P.; Natarajan, J. K.; Alumasa, J.; de Dios, A. C.; Roepe, P. D.; Wolf, C. Overcoming Drug Resistance to Heme-targeted Antimalarials by Systematic Side Chain Variation of 7-Chloro-4-aminoquinolines. *J. Med. Chem.* 2008, 51, 1995-1998.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound selected from the group consisting of formula (I), formula (II), and formula (III):

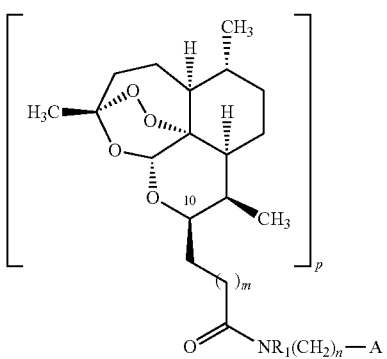

wherein:
m is an integer from 0 to 3;
n is an integer from 0 to 4;
p is 1;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
A is selected from the group consisting of a halogen-substituted phenyl and substituted or unsubstituted heteroaryl; or

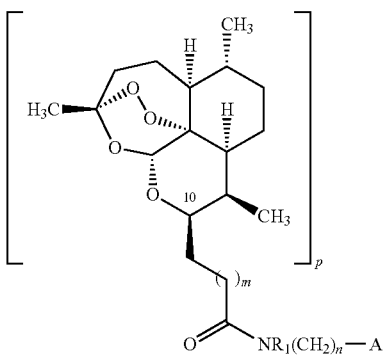

wherein:
m is an integer from 0 to 3;
n is an integer from 0 to 4;
p is an integer from 1 to 2;
$R_1$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
A is $-Si(R_2)_3$, wherein each $R_2$ is independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

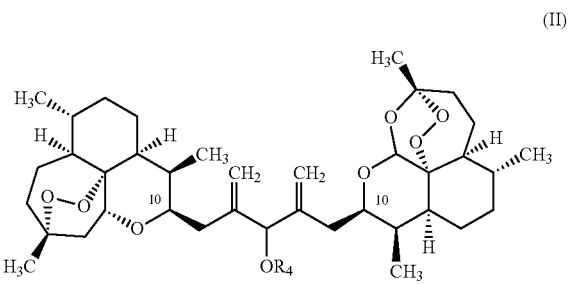

wherein:
$R_4$ is hydrogen or $-C(=O)-Ar$; wherein Ar is substituted or unsubstituted aryl or substituted or unsubstituted heteroaryl;

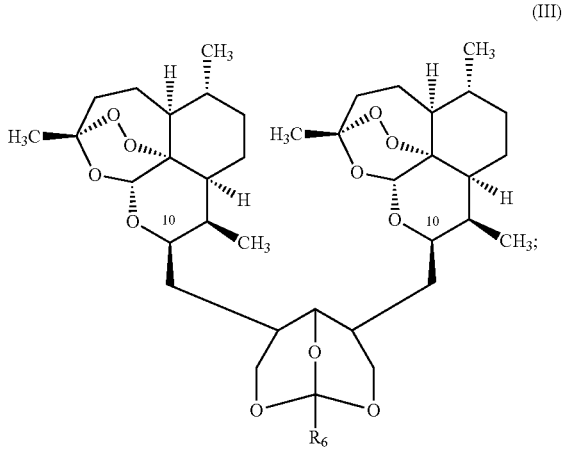

wherein:
$R_6$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, substituted or unsubstituted heteroarylalkyl, $-(CH_2)_t-X$, and $-(CH_2)_sS(O_2)Ar_1$;
wherein s and t are each independently an integer from 1 to 8, X is halogen, and $Ar_1$ is selected from the group consisting of substituted or unsubstituted aryl or substituted or unsubstituted heteroaryl;
or an enantiomer, diastereomer, racemate or pharmaceutically acceptable salt or solvate thereof.

2. The compound of claim 1, wherein the compound is a compound of formula (I) and A is a halogen-substituted phenyl and the compound of formula (I) has the following formula:

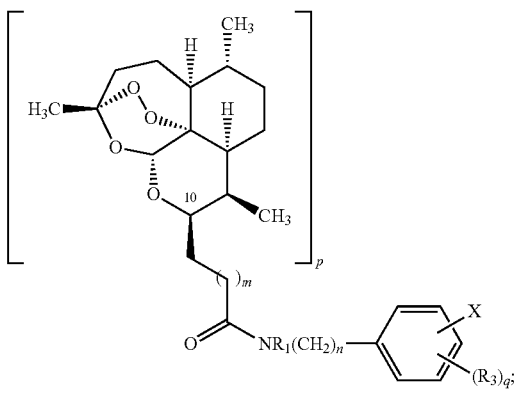

wherein:
p is 1;
q is an integer from 0 to 4;
X is halogen; and
each occurrence of $R_3$ is independently selected from the group consisting of hydroxyl, alkoxyl, amino, mercapto, nitro, halogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, substituted or unsubstituted aryl, substituted or unsubstituted arylalkyl, substituted or unsubstituted heteroaryl, and substituted or unsubstituted heteroarylalkyl.

3. The compound of claim 2, wherein the compound of formula (I) is selected from the group consisting of:

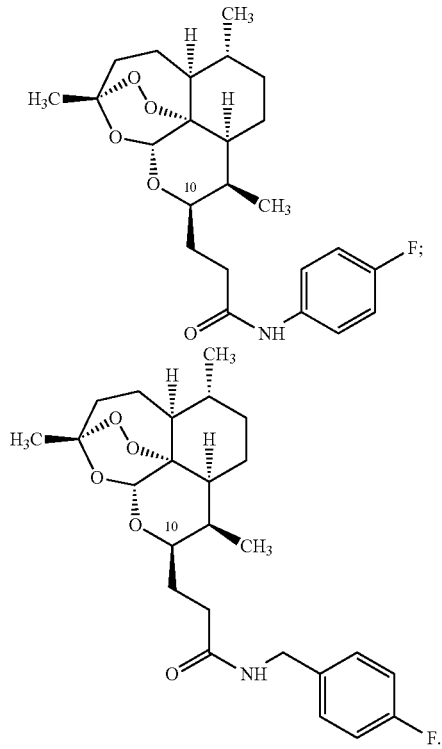

4. The compound of claim 1, wherein the compound is a compound of formula (I) and A is selected from the group consisting of 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

5. The compound of claim 4, wherein the compound of formula (I) is selected from the group consisting of:

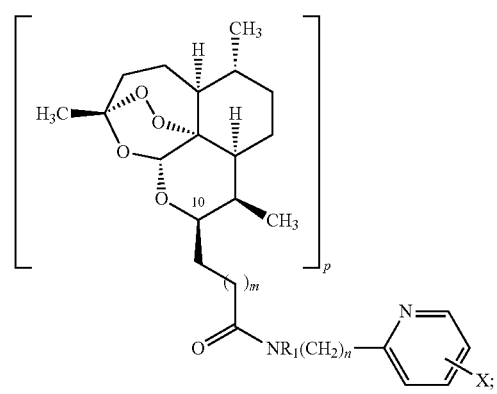

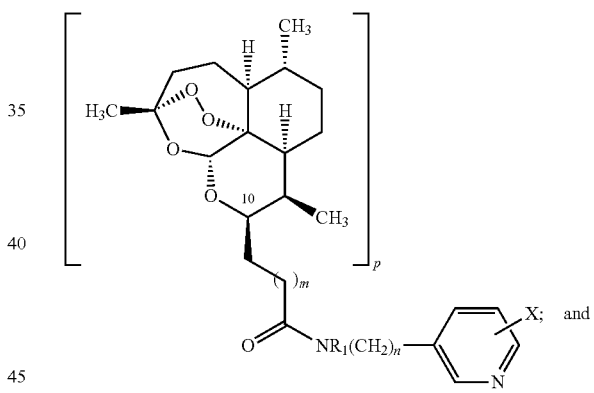

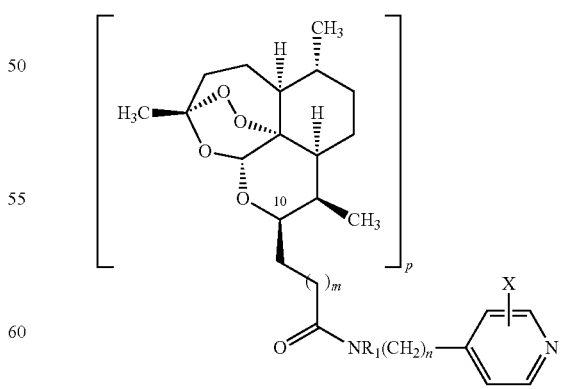

Wherein:
X is halogen and
p is 1.

6. The compound of claim 5, wherein the compound of formula (I) is selected from the group consisting of:
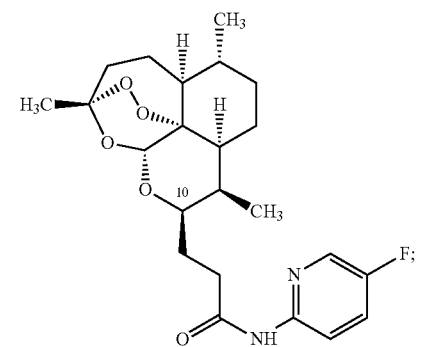
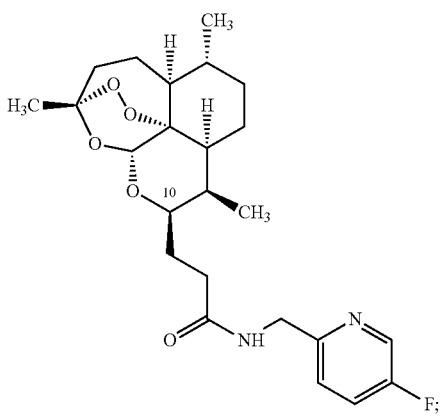
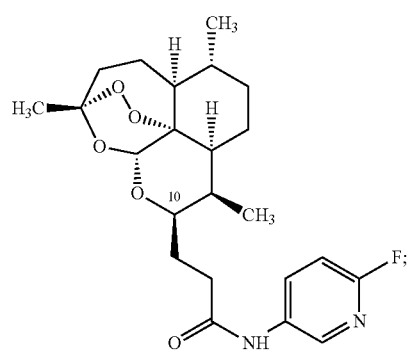
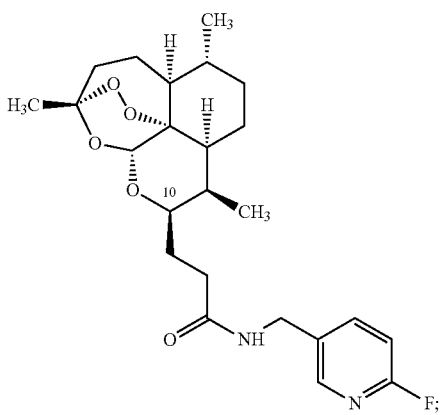
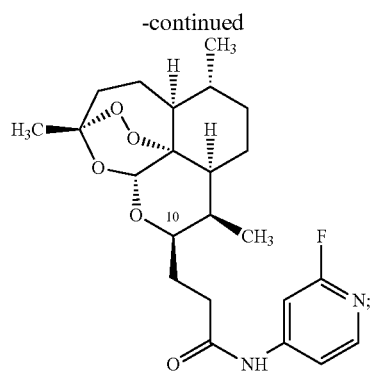
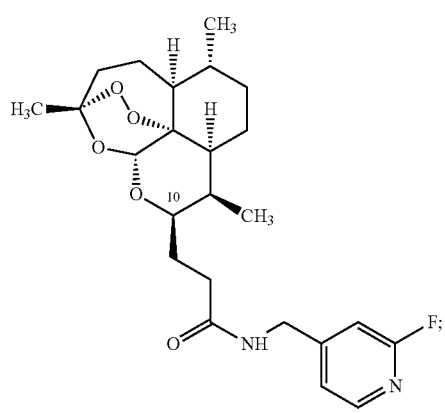
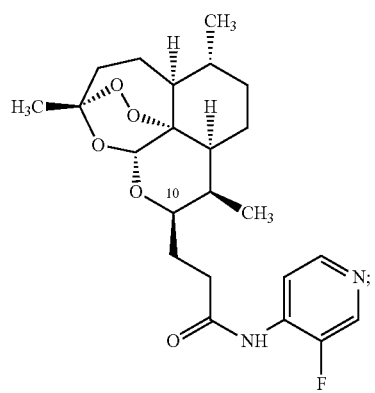
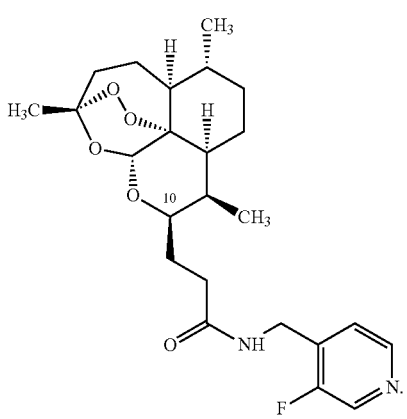
7. The compound of claim 1, wherein the compound is a compound of formula (I) and A is —Si(R$_2$)$_3$ and the compound of formula (I) has the following formula:

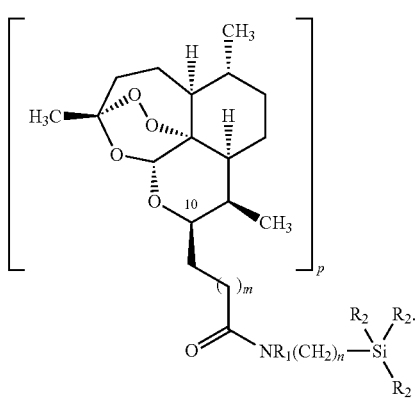

8. The compound of claim 7, wherein the compound of formula (I) is selected from the group consisting of:

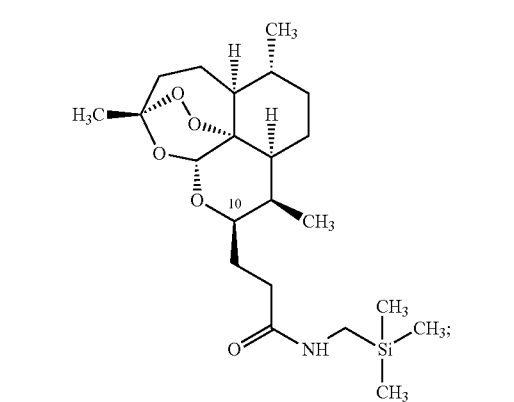

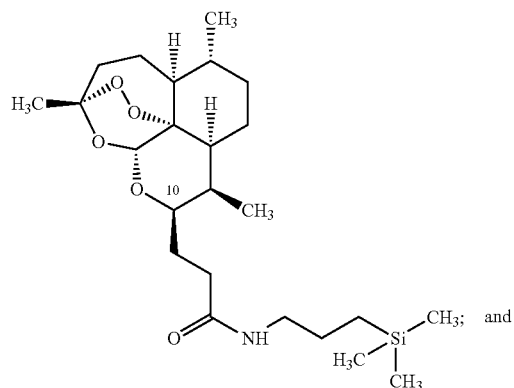

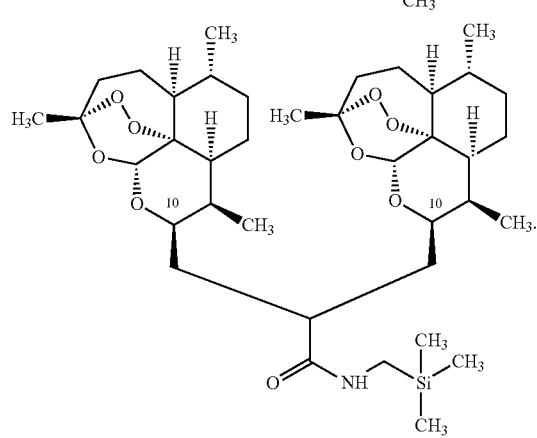

9. The compound of claim 1, wherein the compound is a compound of formula (II) and Ar is selected from the group consisting of:

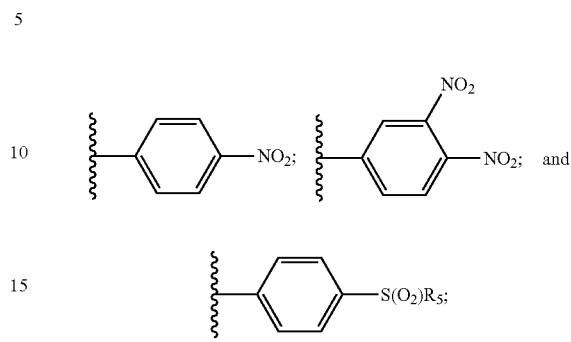

wherein $R_5$ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl.

10. The compound of claim 9, wherein the compound of formula (II) is selected from the group consisting of:

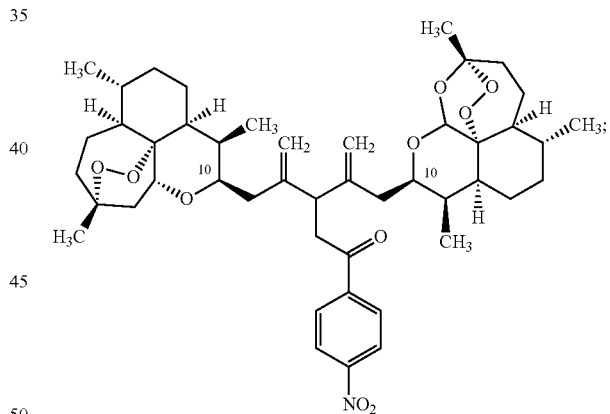

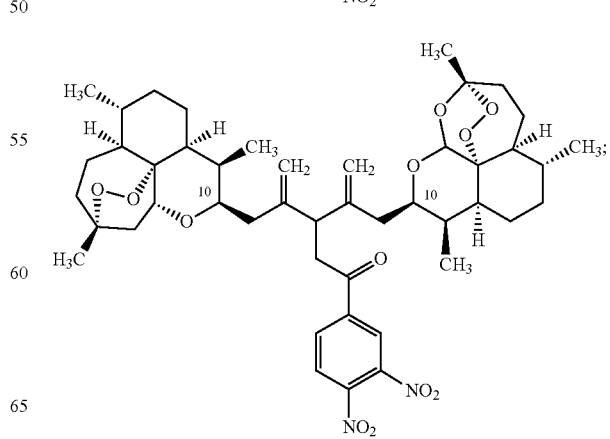

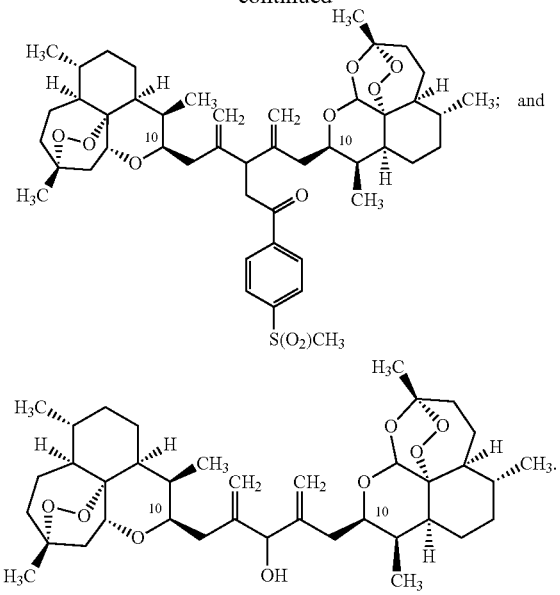

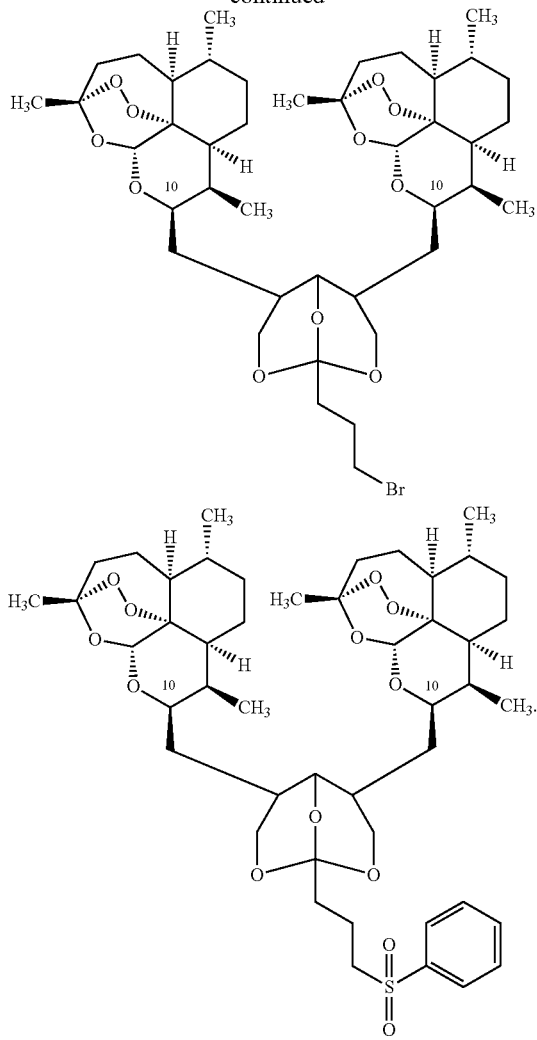

11. The compound of claim 1, wherein the compound is a compound of formula (III) and $R_6$ is selected from the group consisting of hydrogen, aryl or substituted aryl, —$(CH_2)_t$—X, and —$(CH_2)_tS(O_2)Ar_1$.

12. The compound of claim 11, wherein the compound of formula (III) has a structure selected from the group consisting of:

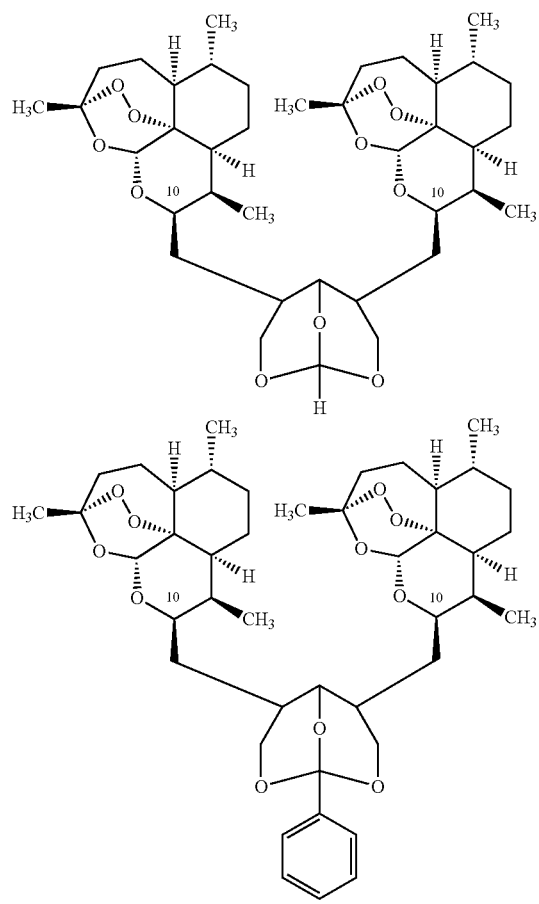

13. A pharmaceutical composition comprising a compound of claim 1.

14. A method for controlling or treating an infectious disease comprising a plasmodia parasite infection in a subject in need of such treatment, comprising administering to the subject a therapeutically-effective amount of a compound selected from the group consisting of formula (I), formula (II), and formula (III):

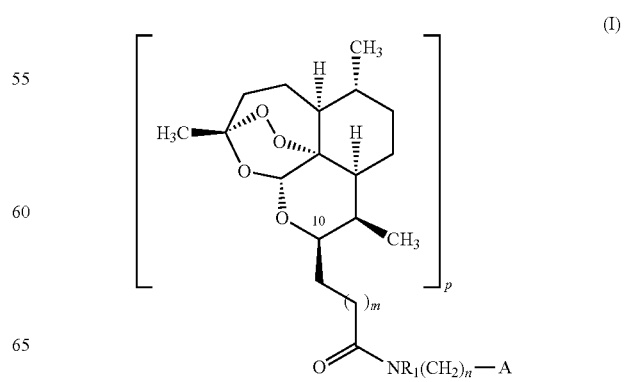

wherein:
 m is an integer from 0 to 3;
 n is an integer from 0 to 4;
 p is 1;
 R₁ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
 A is selected from the group consisting of a halogen-substituted phenyl and substituted or unsubstituted heteroaryl or

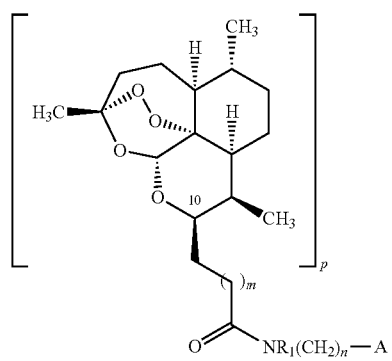

(I)

wherein:
 m is an integer from 0 to 3;
 n is an integer from 0 to 4;
 p is an integer from 1 to 2;
 R₁ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;
 A is —Si(R₂)₃, wherein each R₂ is independently selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, and substituted or unsubstituted heteroarylalkyl;

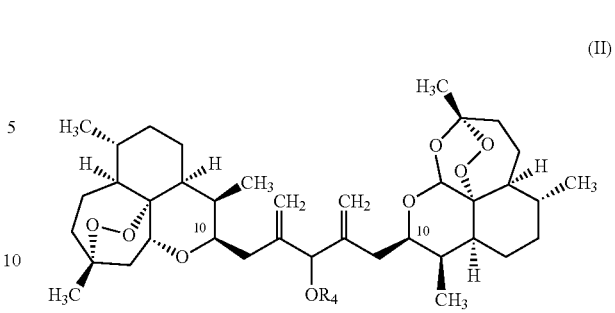

(II)

wherein:
 R₄ is hydrogen or —C(=O)—Ar; wherein Ar is substituted or unsubstituted aryl or substituted or unsubstituted heteroaryl;

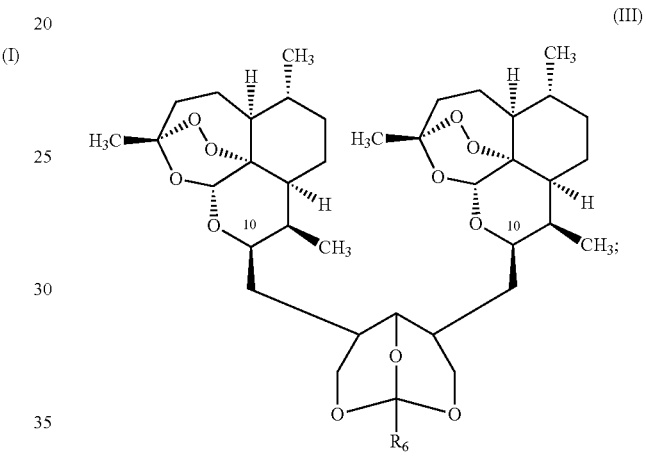

(III)

wherein:
 R₆ is selected from the group consisting of hydrogen, substituted or unsubstituted alkyl, substituted or unsubstituted heteroalkyl, perfluoroalkyl, substituted or unsubstituted cycloalkyl, substituted or unsubstituted heterocycloalkyl, alkenyl, alkynyl, hydroxyl, alkoxyl, substituted or unsubstituted aryl, substituted or unsubstituted arylalkyl, substituted or unsubstituted heteroaryl, substituted or unsubstituted heteroarylalkyl, —(CH₂)ₛ—X, and —(CH₂)ₜS(O₂)Ar₁;
 wherein s and t are each independently an integer from 1 to 8, X is halogen, and Ar₁ is selected from the group consisting of substituted or unsubstituted aryl or substituted or unsubstituted heteroaryl;
 or an enantiomer, diastereomer, racemate or pharmaceutically acceptable salt or solvate thereof.

15. The method of claim 14, further comprising administering to the subject a quinoline anti-malarial drug concurrently or sequentially with the compound of formula (I), formula (II), or formula (III).

16. The method of claim 15, wherein the quinoline anti-malarial drug is selected from the group consisting of chloroquine, quinine, mefloquine, and primaquine.

* * * * *